(12) United States Patent
Saneii

(10) Patent No.: US 10,672,507 B1
(45) Date of Patent: Jun. 2, 2020

(54) SYSTEMS AND METHODS FOR FACILITATING INTERACTIONS BETWEEN TELEVISION SETS AND PERSONAL COMPUTING DEVICES

(71) Applicant: INDEPENDA, INC., San Diego, CA (US)

(72) Inventor: Kian Saneii, San Diego, CA (US)

(73) Assignee: Independa, Inc., San Diego, CA (US)

( * ) Notice: Subject to any disclaimer, the term of this patent is extended or adjusted under 35 U.S.C. 154(b) by 847 days.

(21) Appl. No.: 15/135,396

(22) Filed: Apr. 21, 2016

Related U.S. Application Data

(63) Continuation-in-part of application No. 13/345,596, filed on Jan. 6, 2012, now abandoned.

(60) Provisional application No. 61/430,826, filed on Jan. 7, 2011, provisional application No. 61/558,130, filed on Nov. 10, 2011.

(51) Int. Cl.
| | |
|---|---|
| G06Q 10/00 | (2012.01) |
| G16H 10/60 | (2018.01) |
| G06F 19/00 | (2018.01) |
| G16H 40/63 | (2018.01) |
| G16H 10/20 | (2018.01) |

(52) U.S. Cl.
CPC .......... *G16H 10/60* (2018.01); *G06F 19/326* (2013.01); *G06F 19/3418* (2013.01); *G06F 19/3481* (2013.01); *G16H 10/20* (2018.01); *G16H 40/63* (2018.01)

(58) Field of Classification Search
CPC ....... G06F 19/00; G06F 19/3418; G09B 5/06; A61B 5/044
USPC ................................ 705/2; 725/34; 600/300
See application file for complete search history.

(56) References Cited

U.S. PATENT DOCUMENTS

| | | | |
|---|---|---|---|
| 5,933,136 A | 8/1999 | Brown | |
| 6,168,563 B1 | 1/2001 | Brown | |
| 7,871,376 B2 * | 1/2011 | Brown | A61B 5/044 600/300 |
| 2002/0099276 A1 | 7/2002 | Schmidt et al. | |
| 2006/0253301 A1 | 11/2006 | Simms et al. | |
| 2008/0004904 A1 | 1/2008 | Tran | |

(Continued)

OTHER PUBLICATIONS

Google patents search, Sep. 26, 2018 (Year: 2018).*

(Continued)

*Primary Examiner* — Dilek B Cobanoglu
(74) *Attorney, Agent, or Firm* — Thibault Patent Group

(57) ABSTRACT

A system and method may be provided for facilitating interactions between television sets and personal computing devices. The system may comprise one or more physical servers configured to be communicatively coupled with one or more television sets including a first television set and one or more personal computing devices including a first personal computing device. The servers may comprise one or more hardware processors configured to receive first care management instructions and data concerning the status of a care recipient associated with the first television set via a first user interface visually presented via a first hardware display of the first television set. The first user interface may be laid over television content such that the first user interface is presented regardless of selected channel or input source and such that presentation of television content is not paused when the first user interface is presented by the first television set.

28 Claims, 27 Drawing Sheets

(56) References Cited

U.S. PATENT DOCUMENTS

| | | | |
|---|---|---|---|
| 2008/0242951 A1 | 10/2008 | Jung et al. | |
| 2008/0242952 A1 | 10/2008 | Jung et al. | |
| 2008/0300917 A1* | 12/2008 | Ryan | G06F 19/3418 705/2 |
| 2009/0275807 A1 | 11/2009 | Sitzman et al. | |
| 2010/0115548 A1* | 5/2010 | Leyvi | G09B 5/06 725/34 |
| 2010/0167801 A1 | 7/2010 | Karkanias et al. | |
| 2010/0222649 A1 | 9/2010 | Schoenberg | |
| 2011/0307268 A1* | 12/2011 | Burdea | G06F 19/00 705/2 |

OTHER PUBLICATIONS

Google Patent Search for "Remote patient treatment and current status an analyze data and fame interface and performance," dated Jun. 24, 2014; 2 pages.

Google Patent Search for "Healthcare provider control patient access and patient device," dated Feb. 3, 2015; 2 pages.

* cited by examiner

SYSTEMS AND METHODS FOR FACILITATING INTERACTIONS BETWEEN TELEVISION SETS AND PERSONAL COMPUTING DEVICES

CROSS-REFERENCE TO RELATED APPLICATIONS

This present application is a continuation-in-part of U.S. patent application Ser. No. 13/345,596, filed Jan. 6, 2012, entitled "SYSTEMS AND METHODS FOR INTEGRATED CARE MANAGEMENT," which claims the benefit of U.S. Provisional Patent Application No. 61/430,826, filed Jan. 7, 2011, entitled "CALENDARING SOFTWARE WITH INTELLIGENT REMINDERS," as well as U.S. Provisional Patent Application No. 61/558,130, filed Nov. 10, 2011, entitled "SYSTEMS AND METHODS FOR INTEGRATED CARE MANAGEMENT," which are incorporated herein by reference.

FIELD OF THE DISCLOSURE

The present invention is generally related to care management and more specifically to management of care receiver devices by a care provider client and a care management server.

BACKGROUND

Effective care management is important for care providers, such as loved ones or health care professionals, who look after care receivers, such as the elderly, injured or invalids. Advances in health care have improved the life expectancy and comfort of care receivers. However, similar strides have not been made in the realm of care management. This creates a greater demand upon care providers who are entrusted to ensure the comfort, health and security of care receivers.

Situations can arise where a care provider, such as a loved one or relative, is no longer able to effectively manage the care of their care receiver. For example, providing care for the elderly can become increasingly difficult as the elderly lose independence with age. When the difficulty for care providers to look after their care receivers becomes too burdensome, the responsibility for caring for care receivers is often performed by professionals or specialized care environments such as nursing homes. However, utilization of care professionals and/or specialized care environment can increase the financial cost of care and in some cases the emotional burden of no longer being able to personally take care of a care receiver such as a loved parent, relative or friend.

SUMMARY

Systems and methods for managing the care of care receivers using a care management system are disclosed. One embodiment includes a care management system including a care management server configured to communicate with at least one care provider client, where the care provider client is configured to provide a user interface for receiving care management instructions; where the care management server is configured to receive care management instructions from the at least one care provider client and store the care management instructions in a care management database; receive data concerning the status of a care recipient and store the received data concerning the status of the care recipient in the care management database; analyze the data concerning the status of the care recipient within the care management database in accordance with the care management instructions; and send notifications to the care provider client based upon the analysis of the care management database.

In a further embodiment, the care management server is further configured to receive data concerning the status of a care recipient using automated user interface interactions via a telephone, and send automatically generated notifications to the telephone based upon the analysis of the care management database.

In another embodiment, the care management server is further configured to receive data concerning the status of a care recipient via a care receiver client, and send notifications to the care to the care receiver client based upon the analysis of the care management database.

In a still further embodiment, the care receiver client is configured to access content servers, and the care management server is configured to restrict the content servers that the care receiver client can access.

In still another embodiment, the care receiver client is configured to: display a game user interface; record game performance; and send game performance data to the care management server; and the care management server is further configured to: receive game performance data from the care receiver client and store the game performance data in the care management database; analyze the game performance data; and send a notification to a care provider client in response to the analysis detecting a decline in game performance.

In a yet further embodiment, the care management server is further configured to receive data concerning the status of a care recipient via a care receiver sensor.

In yet another embodiment, the care management server is further configured to communicate with at least one of a care receiver client, a care receiver sensor and a care provider client via the Internet.

In a further embodiment again, the at least one of a care receiver client and a care receiver sensor are configured to connect to the Internet using a wireless hub.

In an embodiment again, the care management server is further configured to receive data concerning the status of a care recipient via at least one of a care receiver client, and a care receiver sensor, and the care management server is configured to update the configuration settings of the at least one of a care receiver client and a care receiver sensor based upon the analysis of the data concerning the status of the care recipient in the care management database.

In a further additional embodiment at least one of a care provider client, a care receiver client, and a care receiver sensor are configured to intermittently synchronize with the care management server.

In another additional embodiment, the care management server receives scheduling data from a care receiver client.

In a still yet further embodiment, the care management database includes a database of pharmaceuticals.

In still yet another embodiment, the care management server is further configured to analyze the data within the care management database to generate a timeline of upcoming notifications, and send the timeline of upcoming notifications to at least one of a care receiver client and a care provider client, which displays a timeline of upcoming notifications via a user interface.

In a still further embodiment again, the care management server is configured to analyze the data within the care management database and send escalated notifications based upon the care management instructions stored in the care management database.

In still another embodiment again, the care management server is further configured to store data concerning the status of a plurality of care recipients in the care management database, and perform analytics to detect patterns that can be used to detect an increased likelihood of a particular status for a specific care recipient in the future.

A still further additional embodiment includes a method of managing the care of care receivers using a care management server, the method including: receiving care management instructions from a care provider client using a care management server and storing the care management instructions in a care management database; collecting data concerning the status of a care recipient using a care management server and storing the data concerning the status of the care recipient in the care management database; analyzing the data concerning the status of the care recipient within the care management database in accordance with the care management instructions stored in the care management database; and sending notifications to the care provider client based upon the analysis of the care management database.

A still another additional embodiment includes receiving data concerning the status of a care recipient using automated user interface interactions via a telephone and sending automatically generated notifications to the telephone.

A yet further embodiment again also includes receiving data concerning the status of a care recipient via a care receiver client and sending notifications to the care receiver client.

In yet another embodiment again, the care receiver client is configured to access content servers, and the method further includes restricting the content servers that the care receiver client can access using the care management server.

A yet further additional embodiment further includes: displaying a game user interface using the care receiver client; recording game performance using the care receiver client; sending game performance data to the care management server using the care receiver client; receiving game performance data from the at least one care receiver client using the care management server and storing the game performance data in the care management database; analyzing the game performance data using the care management server; and sending a notification to a care provider client in response to the analysis detecting a decline in game performance using the care management server.

A yet another additional embodiment includes receiving data concerning the status of a care recipient via a care receiver sensor.

A further additional embodiment again includes communicating between the care management server and at least one of a care receiver client, a care receiver sensor and a care provider via the Internet.

An another additional embodiment again includes connecting at least one of a care receiver client, and a care receiver sensor to the Internet via a wireless hub.

A still yet further embodiment again includes: receiving data concerning the status of a care recipient via at least one of a care receiver client, and a care receiver sensor using the care management server; and updating the configuration settings of the at least one of a care receiver client and a care receiver sensor based upon the analysis of the data concerning the status of the care recipient in the care management database using the care management server.

A still yet another embodiment again includes at least one of a care provider client, a care receiver client, and a care receiver sensor intermittently synchronizing with the care management server.

A still yet further additional embodiment includes receiving scheduling data from a care receiver client using the care management server.

In still yet another additional embodiment, the care management database includes a database of pharmaceuticals.

A still yet further additional embodiment again includes analyzing the data within the care management database to generate a timeline of upcoming notifications using the care management server, and sending the timeline of upcoming notifications to at least one of a care receiver client and a care provider client, which displays a timeline of upcoming notifications via a user interface.

A still yet another additional embodiment again includes analyzing the data within the care management database and sending escalated notifications based upon the care management instructions stored in the care management database using the care management server.

An alternate embodiment includes storing data concerning the status of a plurality of care recipients in the care management database, and performing analytics on the data stored in the care management database using a care management server to detect patterns that can be used to detect an increased likelihood of a particular status for a specific care recipient in the future.

DETAILED DESCRIPTION

Figure 1A:
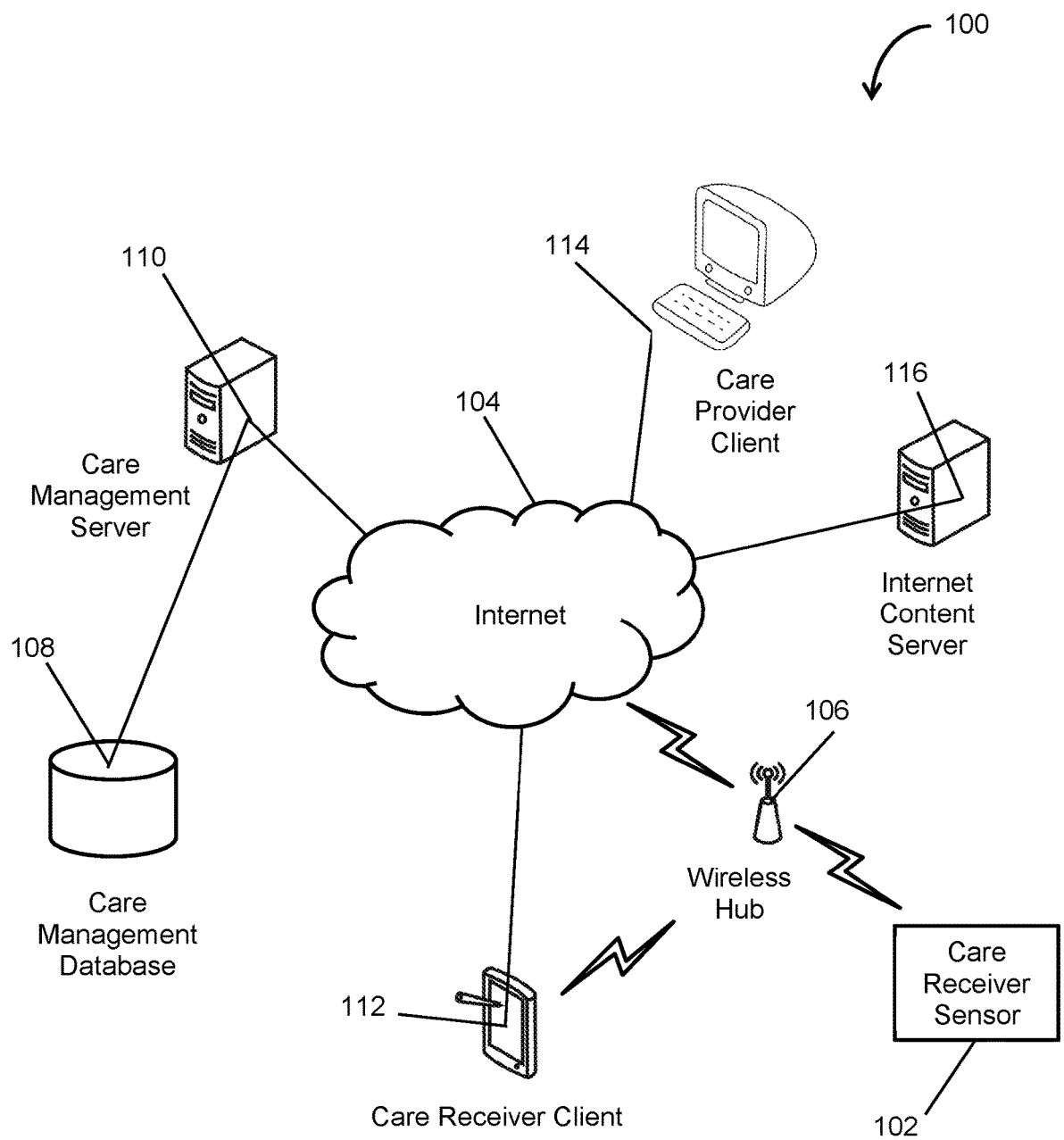
FIG. 1A illustrates a system diagram of a care management system with a care management server managing care receiver clients and sensors with care provider clients in accordance with an embodiment of the invention.

Turning now to the drawings, systems and methods of managing the care of care receivers using a care management system are disclosed. In many embodiments the care management system includes a care management server that receives information from care receiver clients and sensors. Care receiver clients include any device that a care receiver can use to interact with the care management system such as (but not limited to) a tablet, personal computer, Internet connected television, telephone or network connected thermostat. In many embodiments, the care receiver client is a web page, such as an HTML5 page, that can be maintained locally and served via a local server or stored on a remote server. When a user interface is constructed using web technologies, the user interface can be rendered using a web browser rendering engine. Similarly, care provider clients include any device that a care provider can use to interact with the care management system. In various embodiments, a care management server facilitates communication across all care receiver clients and sensors and communication with care provider clients and/or even third parties. By aggregating information at a care management server, the care management system can abstract specific devices and/or sensors and can create an aggregated history of measurements related to the status or condition of a care recipient using a variety of devices. In addition, the care management system can perform analytics upon the data received by the devices. The care management server analyzes data from a care receiver device such as a care receiver sensor or client and the analyzed data can be used to modify and/or update any of the care receiver clients or sensors. The analyzed data can also trigger notifications to a care provider client that is accessible to an individual or a group, such as a doctor's office. The care management server can also access information within a care management database, which stores data accumulated from the care receiver clients and sensors. The care management server can use the information to perform analytics and provide updates and/or notifications based upon the results.

In many embodiments, a care provider client can manage the care of care recipient via the care management server. This can include modifying the settings on care receiver clients and sensors, controlling the type of data sent to the care management server, the settings for the analytics on the care management server, the settings of other the care receiver devices, and the settings for communication between devices.

In numerous embodiments, a care receiver client can access data across a network and/or control care receiver devices. For example, a care receiver client can access general websites, games, video chat, text chat, email, social network forums or even the analytics on a care management server or data in a care management database. A care receiver client can also adjust care receiver devices, including the settings on care receiver clients or sensors. Access for a care receiver client to any other device is generally controlled by a care management server.

In multiple embodiments, a user interface on a care receiver client is a closed environment managed by a care management server with settings determined by a care provider client. However, in other embodiments, the user interface is an open environment that can also be controlled by third parties. In certain embodiments, a user interface can rotate between several high level options such as "Health", "Info", "Fun", "Web", "Social" and "Schedule." Each option can be selected as a list or in a circular fashion where browsing across all categories will loop back to the initial category for browsing. Each option can also have sub options that illustrate another list of options. Additional information is also selectable on a user interface, such as general information, a help button and a search service.

Information bars can also be featured with general information such as the date and time, weather and reminders.

Systems and methods for managing care for a care receiver in accordance with embodiments of the invention are discussed further below.

Care management for care receivers can be dictated by care providers or care receivers and coordinated using a care management server. Care receiver clients can operate while connected to a network such as the Internet through a pervasive connection or offline with periodic or intermittent synching of updates from care receiver clients and sensors with a care management server. A system diagram of a care management system in accordance with an embodiment of the invention is illustrated in FIG. 1A. The care management system 100 includes one or more care receiver sensors 102 connected to the Internet 104 via a wireless hub 106, which can includes a wireless cellular 'cloud' network, mobile broadband, Bluetooth technology or any other wireless connection. The connection is completely or partially wired in certain embodiments using a wired hub. A care receiver client 112 can also be connected with the wireless hub and be accordingly connected with care receiver sensors 102 or the Internet 104. A care management database 108 is connected to a care management server 110.

Figure 1B:
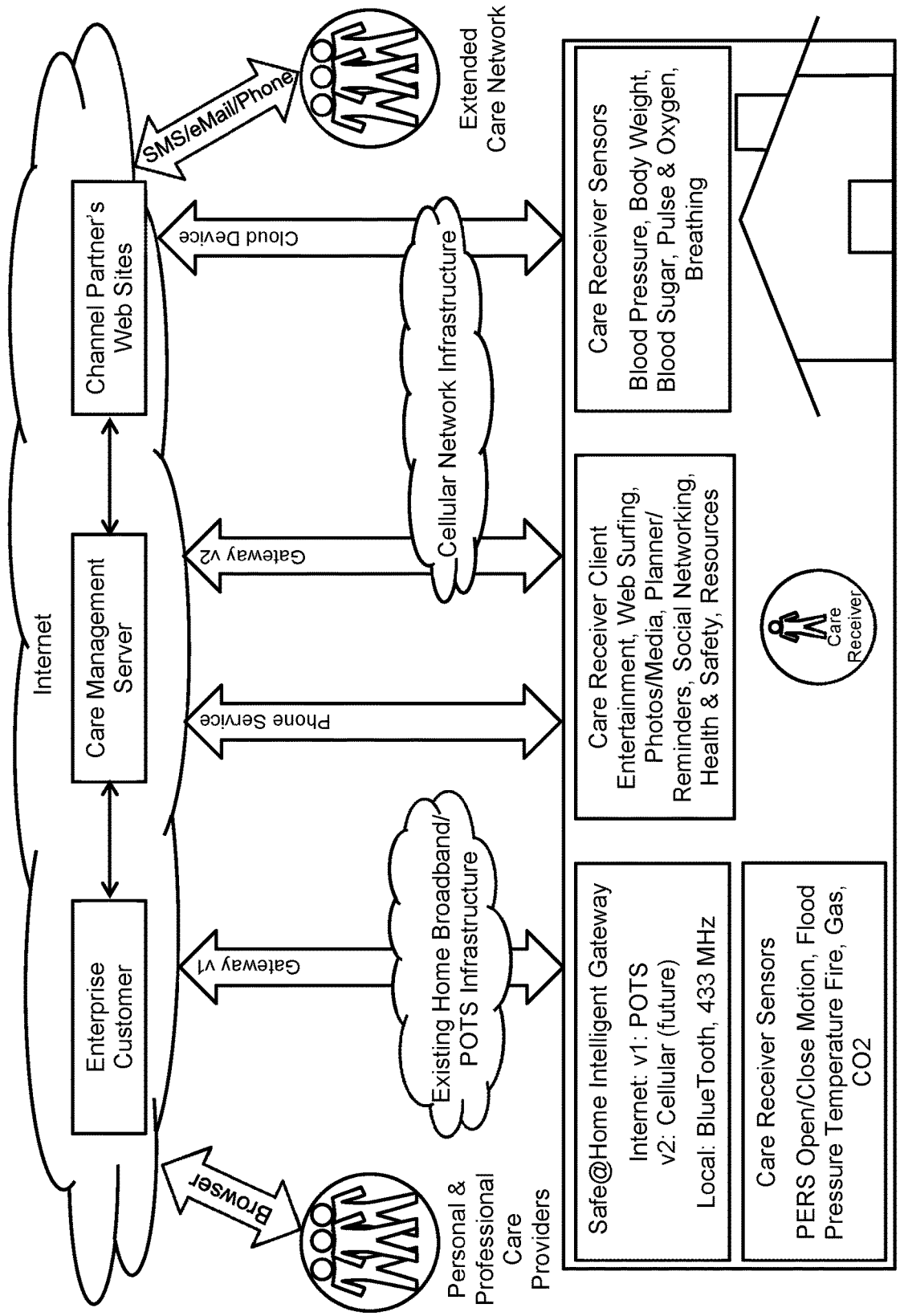
FIG. 1B illustrates a system diagram of a care management system integrating care providers such as professional and personal care providers as well as an extended care network with care receivers in accordance with an embodiment of the invention.
Figure 1C:
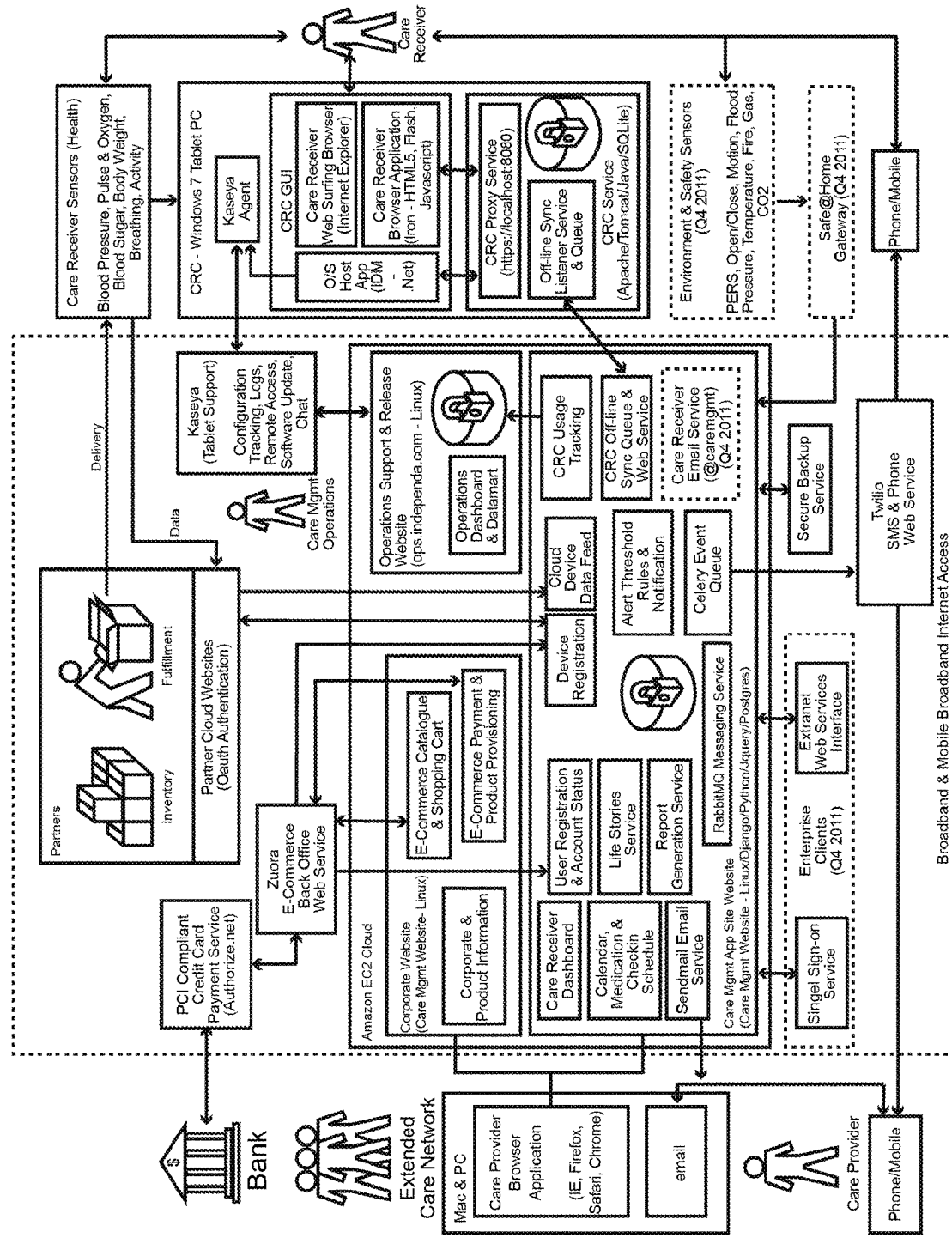
FIG. 1C illustrates a system architecture diagram of a care management system that integrates care providers, such as individual care providers or across an extended area network with care receivers in accordance with an embodiment of the invention.

The Internet 104 connects each of a care management server 110, care receiver client 112, care provider client 114, 3rd party Internet content server 116 and the hub 106 together. System diagrams of similar embodiments are illustrated in FIG. 1B and FIG. 1C. In FIG. 1B, the manner in which the system enables care providers, including personal and professional care providers, and an extended care network to care for a care receiver via a care management server by using care receiver clients and sensors is illustrated. Likewise, as illustrated in FIG. 1C, care providers, either individually or as part of an extended care network can care for a care receiver via a care management system by using care receiver sensors or care receiver clients (CRCs) in accordance with an embodiment of the invention. As can readily be appreciated, care management systems in accordance with embodiments of the system can be deployed by a single care provider network or can be deployed for use by multiple care provider networks. Accordingly, the manner in which the care management system is deployed is largely a function of the requirements of a specific application.

The care management server collects information from the care receiver client and the various care receiver controllers and care receiver sensors. The information collected by the care management server can be utilized in the provision of care to the care recipient including (but not limited to) by providing alerts and/or reminders to the care recipient and/or a care provider and/or third party. In many embodiments, the care receiver controllers and care receiver sensors communicate wirelessly with the hub. In several embodiments, the care receiver controllers and care receiver sensors can utilize wireless communication technology similar to the technology utilized in home security systems. The information collected by the controllers and sensors can then be aggregated and transmitted via a cellular data network by the wireless gateway, which can be implemented using a machine-to-machine communication technology. Examples of machine-to-machine communication technology include cellular network backhaul systems. A network backhaul system can utilize existing cellular network infrastructure and/or broadband service providers. These communication technologies can be implemented in a similar manner to home security solutions, which are a closed and propriety platform unique to each vendor and utilize a home based gateway device with a monthly service charge to route the data and control information between a suite of pre-integrated device sensors and the care management server. These communication technologies can also be facilitated by wireless gateway technology such as 2Net provided by Qualcomm, Incorporated of San Diego, Calif. Qualcomm's 2Net is a privately controlled network with a purpose independent information bridge implemented in a quasi-open architecture.

The care receiver client is typically constrained to limit the user interface available to the care receiver and is configured to communicate to the care management server via the Internet. In many embodiments, the care receiver client relies upon a separate Internet connection to the wireless gateway utilized by the controllers and sensors that also form part of the care receiver's care management system. The manner in which the care management server aggregates information collected via the Internet from controllers and sensors and assists with the provision of care to care receivers in accordance with embodiments of the invention is discussed further below.

A care provider client can provide settings for the care management server. The care management server saves the settings in a care management database and applies the settings on care receiver devices, including (but not limited to) a care receiver client and/or a care receiver sensor. Also, the care receiver client may use a wireless broadband network to communicate with care receiver sensors or a network, such as through Wi-Fi with DSL or Cable Modem Internet access instead of the gateway device. In several embodiments, the care receiver client devices return data to the care management server, which the care management server can store in the care management database. Care receiver clients can operate in online or offline modes. Care receiver clients operating in offline mode store data locally and the care receiver client synchronizes with the care management server when online.

The care management server can perform analytics upon the data in the care management database to determine when to send notifications to the care receiver client, care provider client or a third party including an Internet content server. For example, game performance (potentially indicative of cognitive function) in games played via the user interface of a client receiver device can be sent to a care management server and logged in a care management database. The care management server can perform analytics on the game performance to determine if there is abnormal performance or any other characteristic that triggers a notification. If a notification is triggered, the notification can be sent to a care provider client or via any of a variety of communication technologies including but not limited to care provider client dashboard status, email, SMS, or automated telephone message.

In many embodiments, the care management server facilitates communication between the devices, including data exchange, analytics of data, notification and authorization to access data. In many embodiments, communication between care provider clients and care receiver sensors are routed through the care management server, which stores the settings that the care receiver controller is running in a care management database. Likewise, data exchange between care receiver devices and a care provider client is routed through a care management server which stores the data from the care receiver sensor in a care management database that can be relayed back to the care provider client. In several embodiments, the care management server controls the care receiver client's access to data and applications, such as web email services or videoconferencing applications. In many embodiments, the access granted to a care receiver client by the care management server can be configured by the care provider client.

In several embodiments, the analysis of care receiver device data can include analysis of care receiver device data stored in the care management server to determine whether any dangerous or undesirable condition is present, such as (but not limited to) a care receiver's house being too cold, an open door, a trend of poor performance on games or missing an appointment on the care receiver's calendar. Notifications can include notifying a care provider client or third party when situations of interest, including dangerous or undesirable conditions occur.

In numerous embodiments, the care provider client determines the settings of the care management server and receives updates from the care management server. The care provider client can create settings on the care management server. These settings include the user interface on a care receiver client as well as the data that a care receiver client can access, the settings on care receiver controllers, the analytics performed by a care management server and the types of notifications generated by the care management server.

Figure 1D:
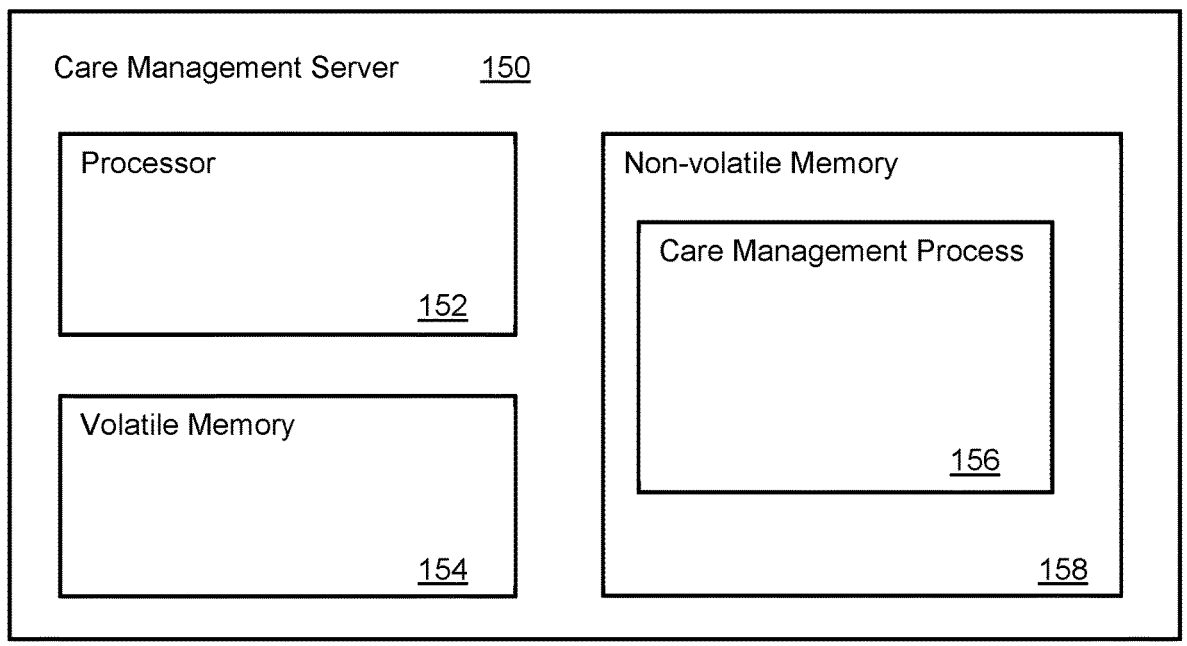
FIG. 1D illustrates a care management server with a processor, volatile memory and non-volatile memory including a care management process in accordance with an embodiment of the invention.

Care management servers in accordance with many embodiments of the invention can load a care management process as machine readable instructions from non-volatile memory stored in a care management server. A care management process loaded from non-volatile memory configures a processor to manage the care of care receivers in accordance with an embodiment of the invention is illustrated in FIG. 1D. The care management server 150 includes a processor 152, volatile memory 154 and non-volatile memory 158 that includes a care management process 156. In the illustrated embodiment, the non-volatile memory is a machine readable media that is utilized to store the machine readable instructions that configure the processor. The non-volatile memory 158 contains the instructions (156), as a care management process 156, utilized to configure the processor 152 of a care management server to care for a care receiver. In many embodiments, care management processes can be loaded from any kind of memory including volatile memory in accordance with many embodiments of the embodiment.

Although a care management system is described above with respect to specific care management servers communicating with a care management database, internet content servers, care provider clients, care receiver clients and care receiver sensors, any of a variety of care management systems can be utilized to manage the care of a care receiver as appropriate to specific applications in accordance with many embodiments of the invention.

Figure 2:
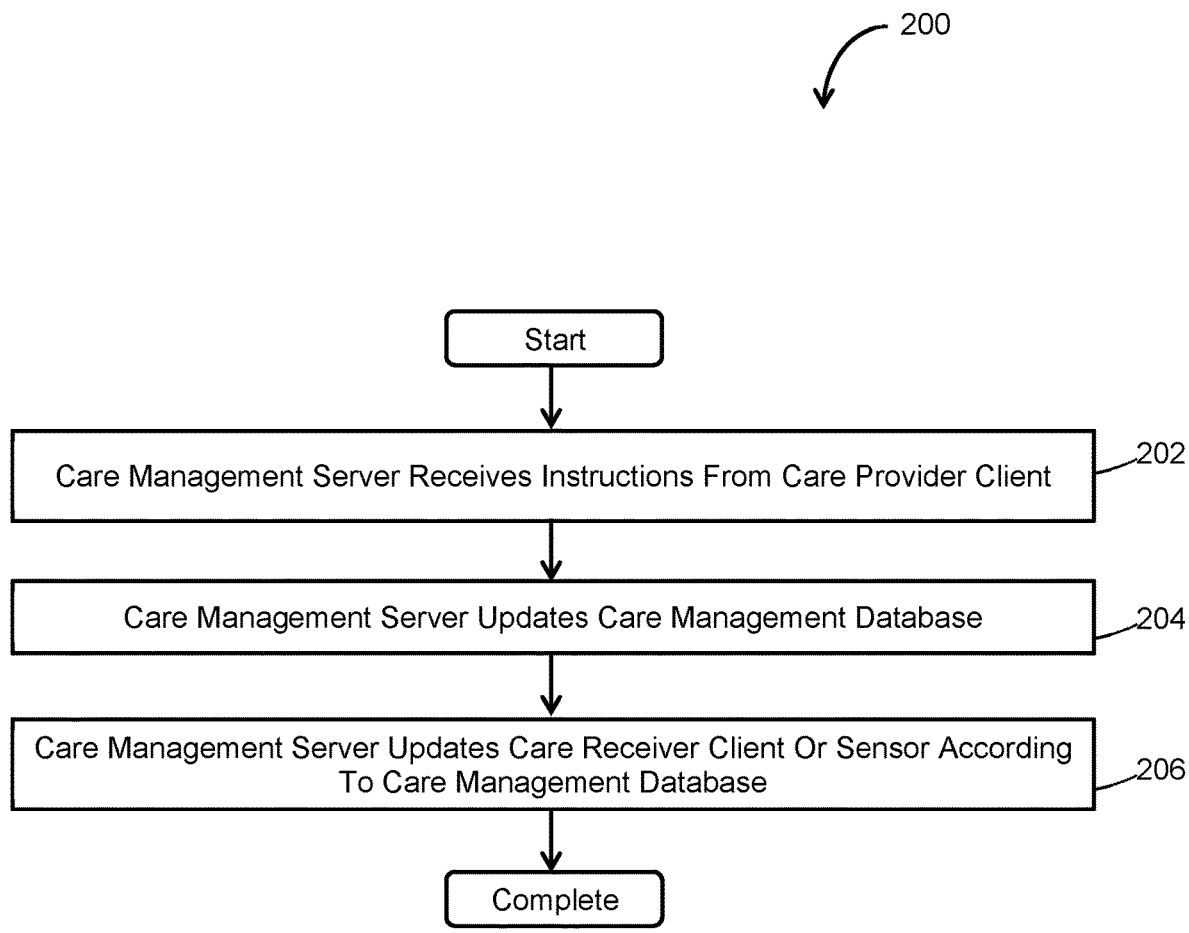
FIG. 2 is a flow chart illustrating a process for updating care receiver devices based upon care provider instructions using a care management server in accordance with an embodiment of the invention.

Care receiver clients and sensors have settings that are determined either by care providers, care receivers or the settings within a care management server. In many embodiments, care receiver clients and sensors are directly updated utilizing the settings on a care receiver server which can be controlled by care provider clients or care receiver clients. A flow chart illustrating a process for updating care receiver clients or sensors based upon care provider instructions using a care management server in accordance with an embodiment of the invention is illustrated in FIG. 2. The process 200 begins with the care management server receiving (202) instructions from a care provider client. After receiving (202) instructions, the care management server updates (204) a care management database. After updating (204) the care management database, the care management server updates (206) a care receiver client, controller and sensor according to settings stored within a care management database.

In many embodiments, the care management server receives instructions from a care provider client, which can include settings for care receiver clients or sensors, such as temperature settings in a care receiver's environment or reminders scheduled in a calendar. In several embodiments, same or similar settings can also be configured by care receiver clients.

In certain embodiments, settings are configured for the care receiver device, including but not limited to settings for games, email accounts, websites to access or contacts that a care receiver can access on a care receiver client. In which case, the care management server updates a care management database of settings for devices. The care management server can then update relevant devices based upon the settings associated with the devices in the care management database, when the devices are next in communication with the care management server.

Figure 3:
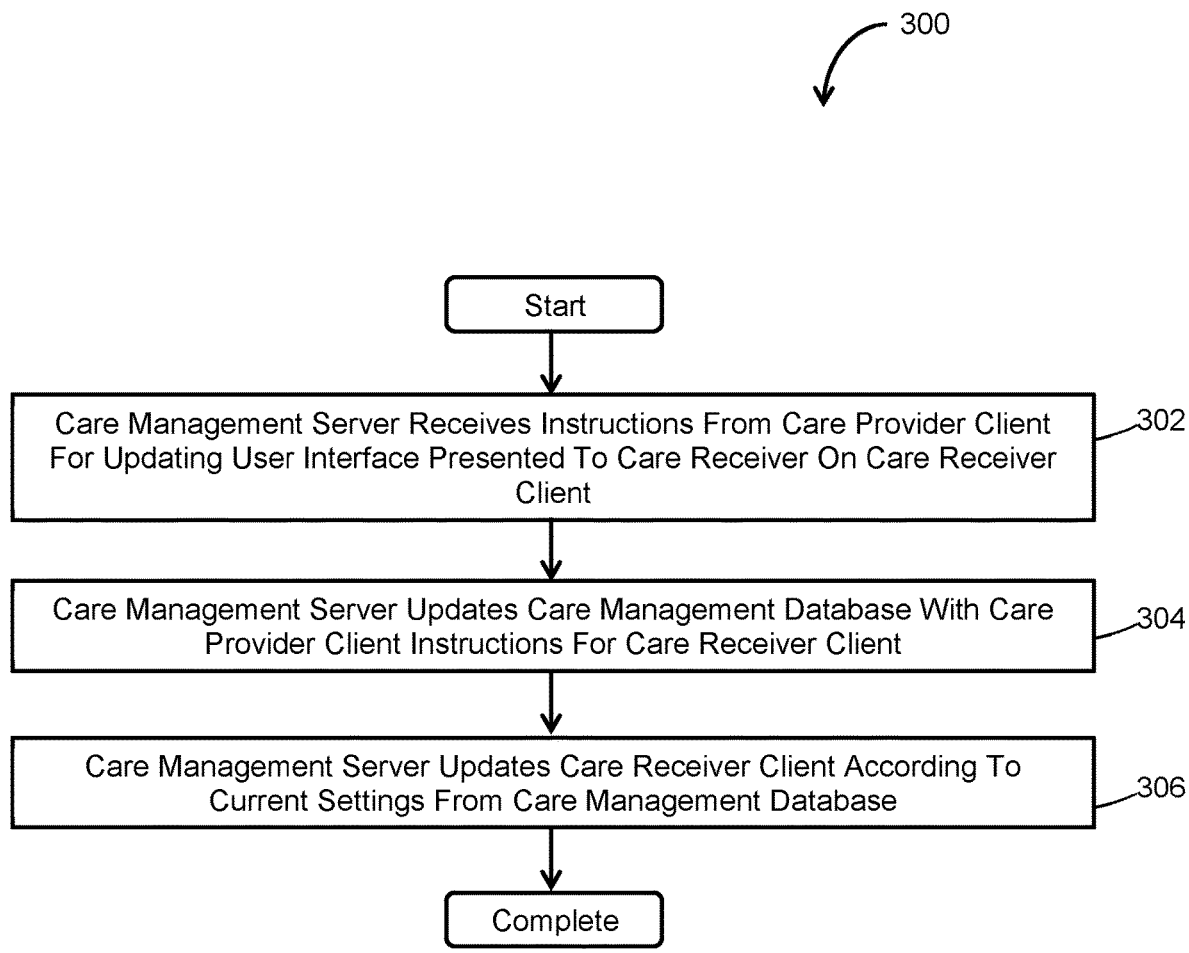
FIG. 3 is a flow chart illustrating a process for presenting a user interface to a care receiver on a care receiver client updated by a care management server in real-time, pre-scheduled, online and offline, based upon instructions received from a care provider client in accordance with an embodiment of the invention.

A further example of a process for updating care receiver clients or sensors using a care management server includes updates to a user interface on a care receiver client in accordance with an embodiment of the invention as illustrated in FIG. 3. The process 300 begins with a care management server receiving (302) instructions from a care provider client for updating a user interface presented to a care receiver on a care receiver client. After the care management server receives (302) instructions, the care management server updates (304) a care management database with the care provider client instructions for the care receiver client. After updating (304) the database, the care management server updates (306) the care receiver client according to the current settings from the care management database.

In many embodiments, a care management server receives instructions for updating an interface for a care receiver on a care receiver client. These instructions can be specific to features on a care receiver client, such as settings for the care receiver client's user interface, games playable on the care receiver client or other features that the care receiver can access on the care receiver client.

In several embodiments, a care receiver client can be a telephone with telephonic or numerical input with auditory instructions from the telephone. The care receiver client can then update the care management database and update other care reliever clients or care provider clients, such as a computer or an Internet connected TV. A process for telephonic input on a care receiver client can include an instruction as to select the data to input into the telephonic care receiver client such as (but not limited to) a care receivers weight, blood pressure, glucose level, pulse or oxygen readings. After the selection of data to input, an instruction is given to input the data numerically via the telephone. A telephonic care receiver client can also be utilized to fill out a questionnaire where data can be entered as a yes or no answer, where a certain numerical input via a telephone key pad is deemed to be a "yes" and another is deemed to be a "no." Confirmation of selections can be made after each part of the process. Additionally, a time limit can be place upon telephonic input of an arbitrary amount such as 10 seconds. Furthermore, validation and error checking can be in place for inputted telephonic data such as whether a plausible weight was entered. In this way, measurements concerning the status of a care recipient can be taken using conventional measurement devices and/or instruments (i.e. devices that do not communicate with a care management server) and the measurements provided to the care management server via a telephone user interface. Furthermore, questions can be asked by the user interface to obtain information that may be used in the normalization of the care recipient status data provided to the care management system. In several embodiments, either care receiver or care provider clients are telephonic. In many embodiments, data collected via automated telephone interaction can be supplemented with data obtained via other sensors. In a number of embodiments, the automated telephone interaction prompts the care recipient to utilize a sensor to provide information to the care management system. The collection of data and the analysis of data by care management systems in accordance with embodiments of the invention is discussed further below.

Care management servers in several embodiments can track and manage reminders for care receivers such as events, meetings or activities. In many embodiments, a care receiver client can record and implement settings and notifications within a schedule stored within a care management database or locally stored within a care receiver client that can synch with a schedule in a care management database.

In several embodiments, the care management server creates and tracks reminders associated with specific medications and/or specific measurements that the care recipient is meant to take using either using sensors collected to the care management server or disconnected sensors that the care recipient uses and then reports the acquired measurements to the care management server via the care recipient client and/or an interactive telephone system. In many embodiments, the care management server receives updates from the care recipient in the manner outlined above and matches the information in the updates to the reminders. For example, receipt of a weight measurement can be utilized to automatically cancel the generation of a reminder to measure weight. In other instances, any of a variety of different updates can be processed by the care management server and utilized to modify and/or cancel generation of reminders.

Scheduling in accordance with numerous embodiments of the invention allows a user to create events related to appointments, and to set reminders for the created events. These reminders can take into account the context of the event, such as automatic modification of reminders based on one or more of traversal distance of the event location from a current location of the care receiver, real time traffic reports or projected traffic based upon time of day, or updated weather reports. In several embodiments, scheduling can be used to create events and invite people including those that do not have access to the same scheduling application used to create the event. Further, the scheduling may generate reminders via different modalities including device-based alerts, messaging, telephone calls, SMS, or e-mail. Scheduling can also feature different escalation points such as when confirmations are not received so that if an e-mail or device based reminder is not responded to within a limited time period (5 minutes for example) it is followed up by a call. In certain embodiments, schedules can be operated offline with data cached and synched with a care management server when a connection with the care management server is achieved.

Figure 4A:
FIG. 4A illustrates a care receiver client graphical user interface displaying a daily medication list in accordance with an embodiment of the invention.
Figure 4B:
FIG. 4B illustrates a care receiver client graphical user interface displaying a weekly schedule of medications in accordance with an embodiment of the invention.

In several embodiments, care receiver clients can inform a care receiver as to the schedule of medications that a care receiver should be taking. FIG. 4A illustrates a daily medication schedule on a care receiver client in accordance with an embodiment of the invention. This medication schedule includes both the medication and the time, status, supply of medication and directions for the administration of the medication. Likewise, FIG. 4B illustrates a weekly medication schedule on a care receiver client in accordance with an embodiment of the invention.

In many embodiments, a care management server receives instructions for updating the medication list on a care receiver user interface. The care management server then sends the updated medication list to the care receiver client. In certain embodiments, if a care receiver client is offline, the care management server will use alternative means, such as a phone or email to remind or alert a care receiver to administer the medication. A care receiver client can also operate offline, such as in certain embodiments where a care receiver client will capture locally acquired data such as inputs to the care receiver device or data from care receiver sensors and cache the data until the care receiver client is next online.

In many embodiments, a care management database includes a database for selecting medications or drugs. This database of drugs is built over time and is based upon relevance such as whether certain drugs are interchangeable with others and can include information concerning uses for certain drugs. In several embodiments, a third party drug database is used to help care providers or care receivers pick from a list of matching drug names as they start entering the drug. In one embodiment, the database thereby makes it easier to enter in a drug name by automatically filling out the name as a user types it in. A user can still enter in a name of a drug if the drug is not in the database and the new drug name is added to the care management database in the cloud. In one embodiment, a new drug is sorted in a database of drugs based on frequency of use of the same drug name by multiple users, such as care providers or care receivers. Assessments of drug use based upon frequency addresses both typographical errors (as even though the intended drug may be in the database, typographical errors may cause the drug name not to appear in the list to be picked) as well as actual drug names, which may be missing from the database. In one embodiment, "Edvil" can be a misspelling of "Advil". "Advil" is a brand of ibuprofen manufactured by Pfizer Incorporated, based in New York City, N.Y. The frequency of entries of "Edvil" will determine whether this new term is added to the database. In one embodiment, if three entries or less occur over a period of six months, the new term is not added to the database of drugs shared by a common care management database, but those three individual users would have the new term in their own list of drugs. However, if more than three people added the new term within six months, this may be a new drug that is not added to the care management database's section for drugs and therefore can be added to a common care management database for multiple users. Although specific numbers of users and periods of time are referenced above, the criteria for adding a new term to the database can be determined based upon the requirements of a specific care management system.

In many embodiments, a care management server manages reminders for events in a schedule. In certain embodiments, a user interface uses a time-line to manage upcoming reminders, distinguishing between events that are closer and farther away in time. In several embodiments, reminders on a care receiver client user interface moves toward a "now" mark on a time-line displayed via the user interface as time goes on. Hitting a "now" option on a care receiver client user interface associated with the reminder can cause a visual reminder of a distant event to move away from "now" and ultimately off the screen. If the reminder is "completed", then the reminder on the user interface moves forward with a checkmark and no further escalations are applied. If not, the lack of completion of the reminder can have escalation rules applied. The escalation rules govern how different alerts are generated that call attention to a task that has not been completed, such as generating alert noise or pop up reminders on a user interface. In many embodiments, failure to confirm that a reminder is "completed" can result in an alert being provided to a care provider by the care management server in the manner discussed above. Notification and alert escalation in accordance with embodiments of the invention is discussed further below.

Figure 5:
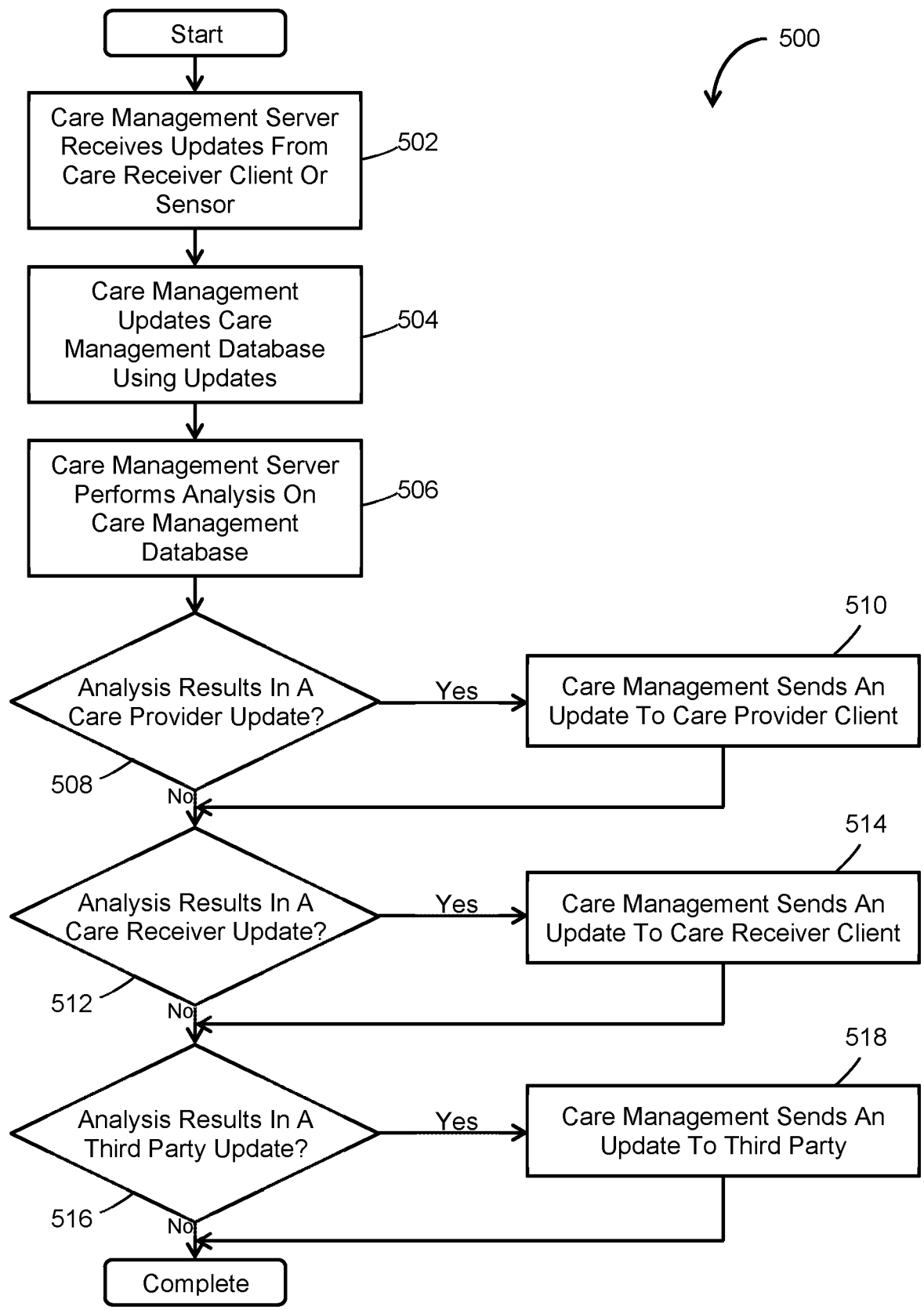
FIG. 5 is a flow chart illustrating a process performed by a care management server using inputs from care receiver clients or sensors where the care management server uses the data to send notifications or updates to a care receiver client, a care provider client or third party in accordance with an embodiment of the invention.

A care management server aggregates data from care receiver clients and sensors, care provider clients and/or third parties for analysis and can generate alerts for and/or update care receiver clients and sensors, care provider clients and third parties in accordance with various embodiments of the invention. The data is typically aggregated within the care management database and analytics can be performed upon the data utilizing the processer in the care management server. A flow chart illustrating a process performed by a care management server to send notifications to a care receiver client or a care provider client in accordance with an embodiment of the invention is illustrated in FIG. 5. The process 500 begins with a care management server receiving an update (502) from a care receiver client or a sensor. After receiving the update (502), the care management server updates (504) a care management database based upon the update (502) from the care receiver client or sensor. After updating a care management database (504), the care management server performs analysis (506) on the care management database. After analyzing (506) the care management database, a decision (508) is made as to whether the analysis necessitates a care provider update. If the analysis directs that a care provider should receive an update, then the care management server sends (510) an update to a care provider client. Another decision (512) is then made as to whether the care receiver should also receive an update. If the analysis result in a care receiver update, then the care management server sends (514) an update to the care receiver client and a decision is made as to whether the analysis results in a third party update. If the analysis results in a third party update, then the care management server sends (518) an update to a third party. If the analysis does not result in a third party update, the then process is complete. As can be appreciated, decisions concerning whether to update various care receivers, care providers, and/or third parties can be made independently.

In many embodiments, the care management server can receive updates from care receiver devices related to changes in the environment, such as temperature changes or time/date changes; or changes in security or well being, such as open/closed doors or unresponsiveness to telephone calls. The care management database stores data from the care receiver devices for analysis that can result in updates for either the care provider, care receiver, or care receiver devices.

In many embodiments, analysis of data in a care management database can incorporate custom thresholds set by a care provider. In certain embodiments, Boolean and value range functions are used that apply a single alert type if a threshold is met. In one embodiment, a set of complex range functions can be set. For example, the range function could incorporate requirements including (but not limited to) where if the inside temperature in a care receiver environment is <70 and bathroom visits yesterday were >10 and the care receiver was inside all day and the fridge door was not opened all day and the care receiver rose out of bed >3 hours past her normal time, then an alert is generated and sent to a care provider client. Alerts can come at different levels indicating the seriousness of the alert. In many embodiments, a red alert can be an alert indicating high seriousness and a green alert can indicate an alert of low seriousness. Combinations of factors can be considered in the generation of alerts. For example, if a care receiver has not picked up a reminder call and the care receiver is indoors and there is no motion >4 hours during the day, then a red alert update is sent to a care provider client. In other embodiments, any of a variety of pieces of information collected via the care receiver devices can be utilized in evaluating whether to generate an alert.

In many embodiments, analysis of data in a care management database can generate threshold escalation. In several embodiments, threshold escalation occurs if the same threshold occurs more than a predetermined number of times defined by a care provider. In which case, the alert can escalate from a current alert level to a higher alert level. For example, in several embodiments, a care receiver failing to step on a scale all day is a yellow alert. However, if the care receiver has not stepped on a scale all day for a certain number of days set by the care provider, such as 3 days, then the alert moves to a higher level. As indicated above, the factors that are considered in generating and escalating alerts can be customized by the care provider via a user interface provided by the care management server.

In several embodiments, analysis of data in a care management database generates multiple alert thresholds. In certain embodiments, escalation moves by multiple threshold levels and not just one threshold level where the analysis detects a significant change. In one embodiment, a situation matching a situation escalation but indicative of a more serious issue, such as an immediate threat to the well being of a care receiver, can move immediately from no alert to the highest alert level.

In a number of embodiments, the data stored in the care management database with respect to a number of care recipients can be used to detect patterns indicative of a likelihood of a particular status. So called "predictive analytics" can be enhanced by combining the status data with healthcare outcome data. In this way, the data can be used to provide notifications of the detection of a pattern associated with a particular status and/or potential healthcare outcome.

Figure 6A:
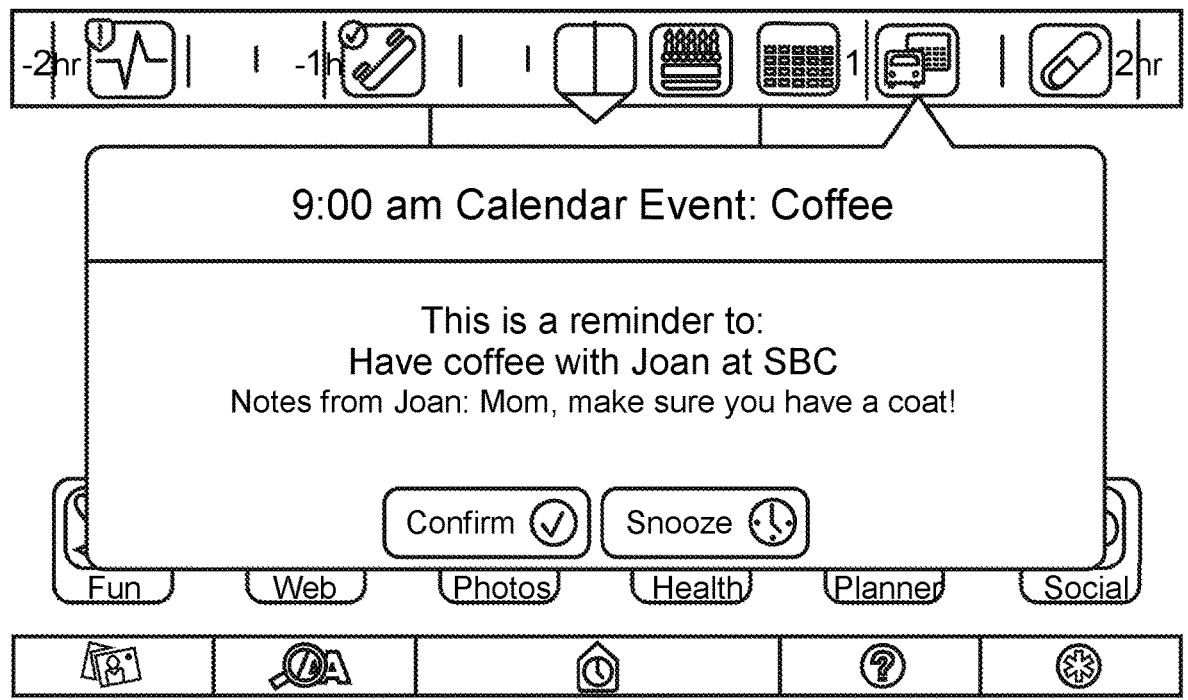
FIG. 6A illustrates a care receiver client graphical user interface displaying a scheduled reminder in accordance with an embodiment of the invention.
Figure 6B:
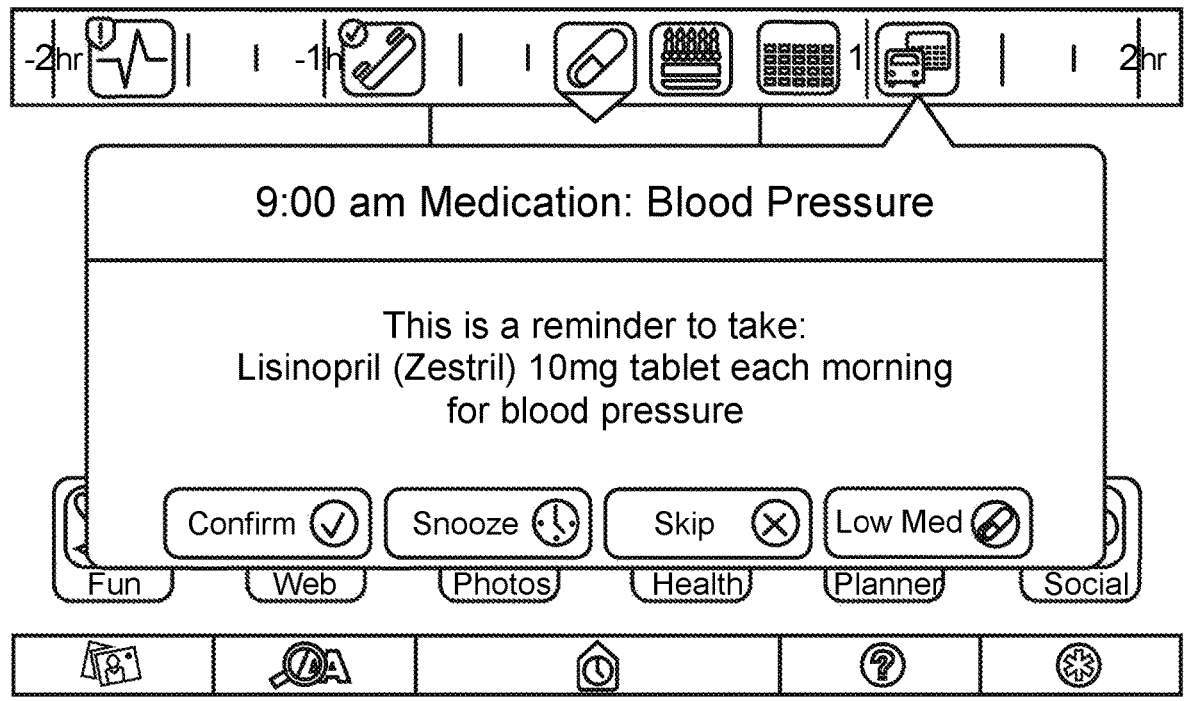
FIG. 6B illustrates a care receiver client user graphical interface displaying a medication reminder in accordance with an embodiment of the invention.

A care receiver client can enable a care receiver to interact with the care management server and can display data of interest for a care receiver in accordance with embodiments of the invention. In numerous embodiments, a care receiver client includes reminders for events or medication for administration to a care receiver. FIG. 6A illustrates the display of a reminder on a care receiver client user interface in accordance with an embodiment of the invention. Likewise, FIG. 6B illustrates the display of a reminder for a care receiver to take medicine in accordance with an embodiment of the invention. In many embodiments, care receiver devices can detect changes or perform periodic updates. For example, in certain embodiments, a care receiver device detects whether the care receiver has sent out oxygen level information. When the care receiver device detects a status of oxygen level information, the care receiver device sends that information to a care management server, which updates a care management database. The care management server then performs analytics determining whether the oxygen level information is absent and if the absence is noteworthy for the care receiver, will send a notification to the care receiver client that will alert the care receiver concerning the need to obtain an oxygen level measurement.

Figure 7:
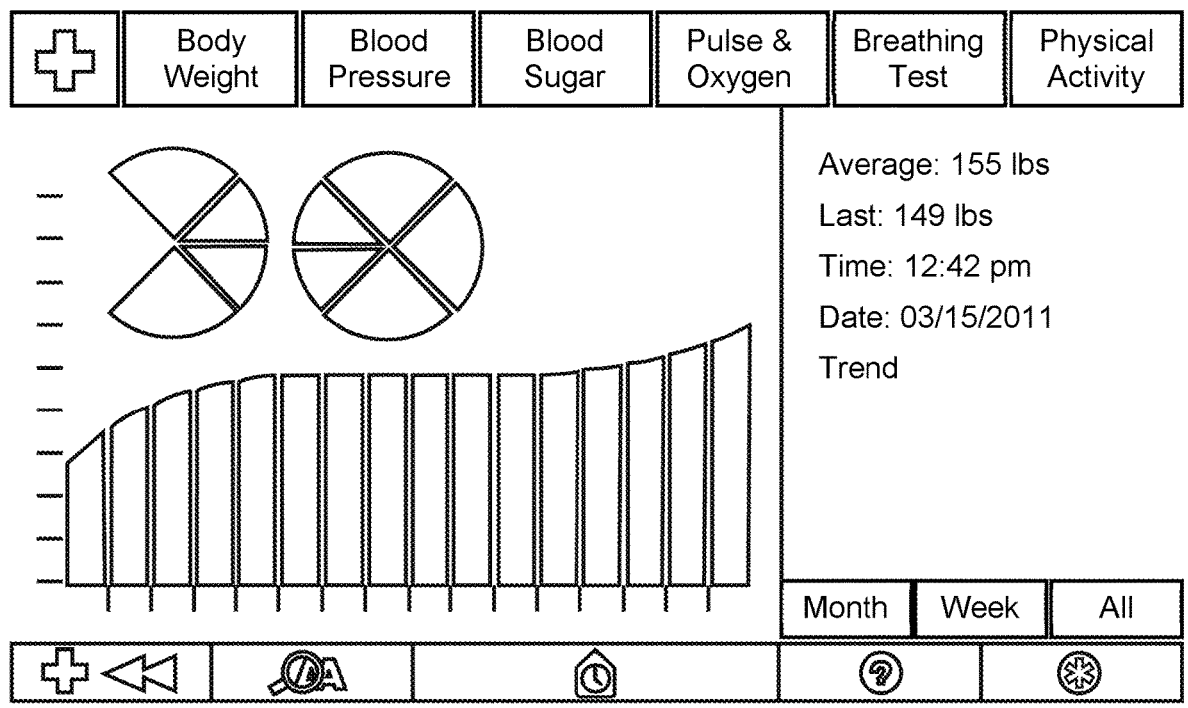
FIG. 7 illustrates a care receiver client user graphical interface displaying data analyzed from care receiver sensors and/or clients in accordance with an embodiment of the invention.

Data of interest to a care receiver can also be displayed on a care receiver client in many embodiments. Data of interest can include the status or updates from care receiver sensors or analyzed data regarding the care receiver. Body weight data concerning a care receiver as displayed on a care receiver client in accordance with an embodiment of the invention is illustrated in FIG. 7. In the illustrated embodiment, details concerning body weight are displayed such as body weight average and the last body weight measurement as well as a graph illustrating body weight measurements plotted across different measurement times. In various embodiments, data of interest can also be displayed on a care provider device or on a third party client.

Figure 8A:
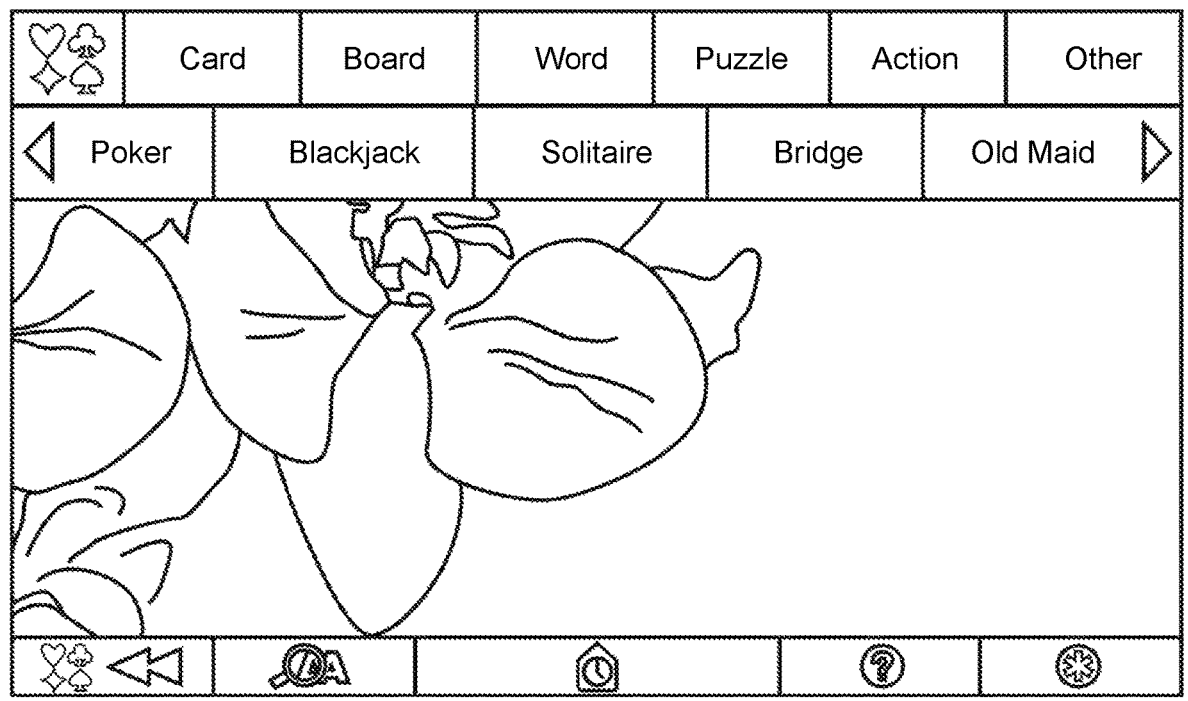
FIG. 8A illustrates a care receiver client user interface displaying a gaming interface in accordance with an embodiment of the invention.
Figure 8B:
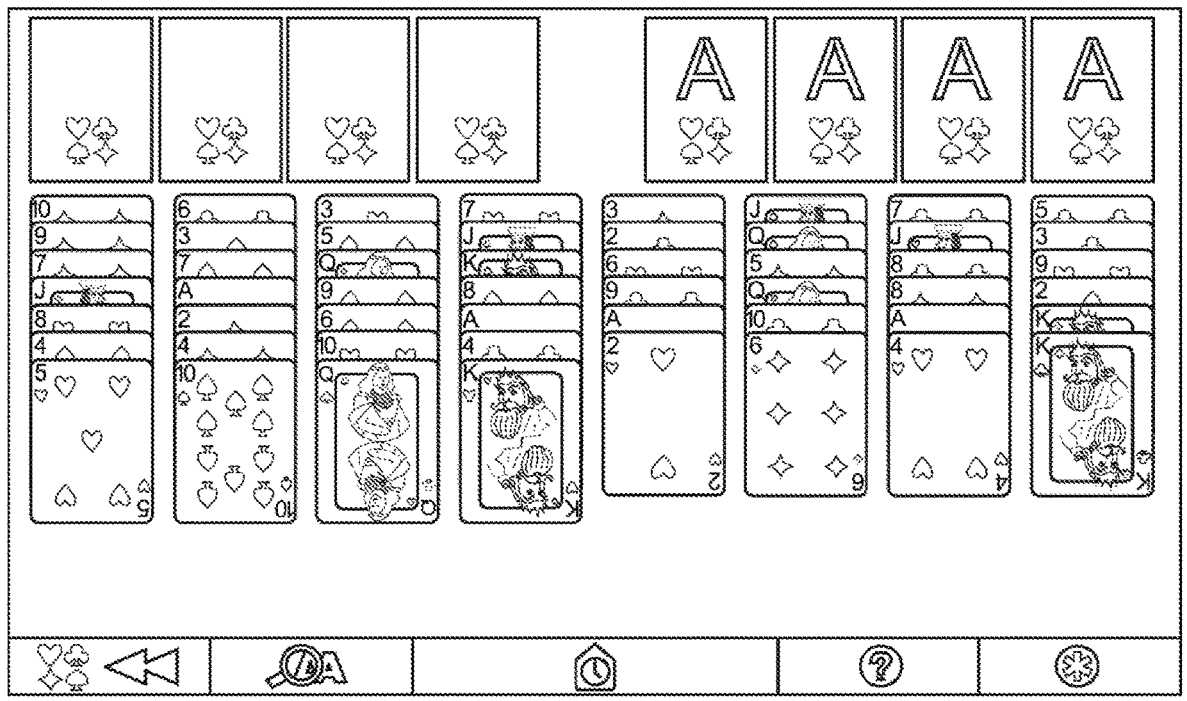
FIG. 8B illustrates a care receiver client user interface displaying a single player card game in accordance with an embodiment of the invention.

Additionally, games can be utilized on a care receiver client for entertainment. A graphical user display of games that a care receiver can play on a care receiver client in accordance with an embodiment of the invention is illustrated in FIG. 8A. In the illustrated embodiment, a care receiver can browse among various different genres and types of games. Additionally, in many embodiments, the cognitive function of a care receiver can be monitored by observing the care receiver's ability at playing various games. A significant drop in performance can often be indicative of a decline in status. In many embodiments, a care receiver can use a care receiver client to play a multiplayer game with other players. The care provider or care management server can set the options for game play such as access to the game or access to game settings. FIG. 8B illustrates a card game played via a care receiver client user interface in accordance with an embodiment of the invention. In the illustrated embodiment, a care receiver can choose to play a single player game of solitaire.

In a number of embodiments, a strong trend of winning followed by a gradual but firm trend of losing games can be indicative of dementia in certain cases. Data from game play can be sent from the care receiver client to a care management server. The care management server can update a care management database with data on game play and perform analysis on the care management database. The analysis can indicate whether an update or an alert should be sent to a care provider. The analysis can also indicate whether a third party should be updated.

Figure 9:
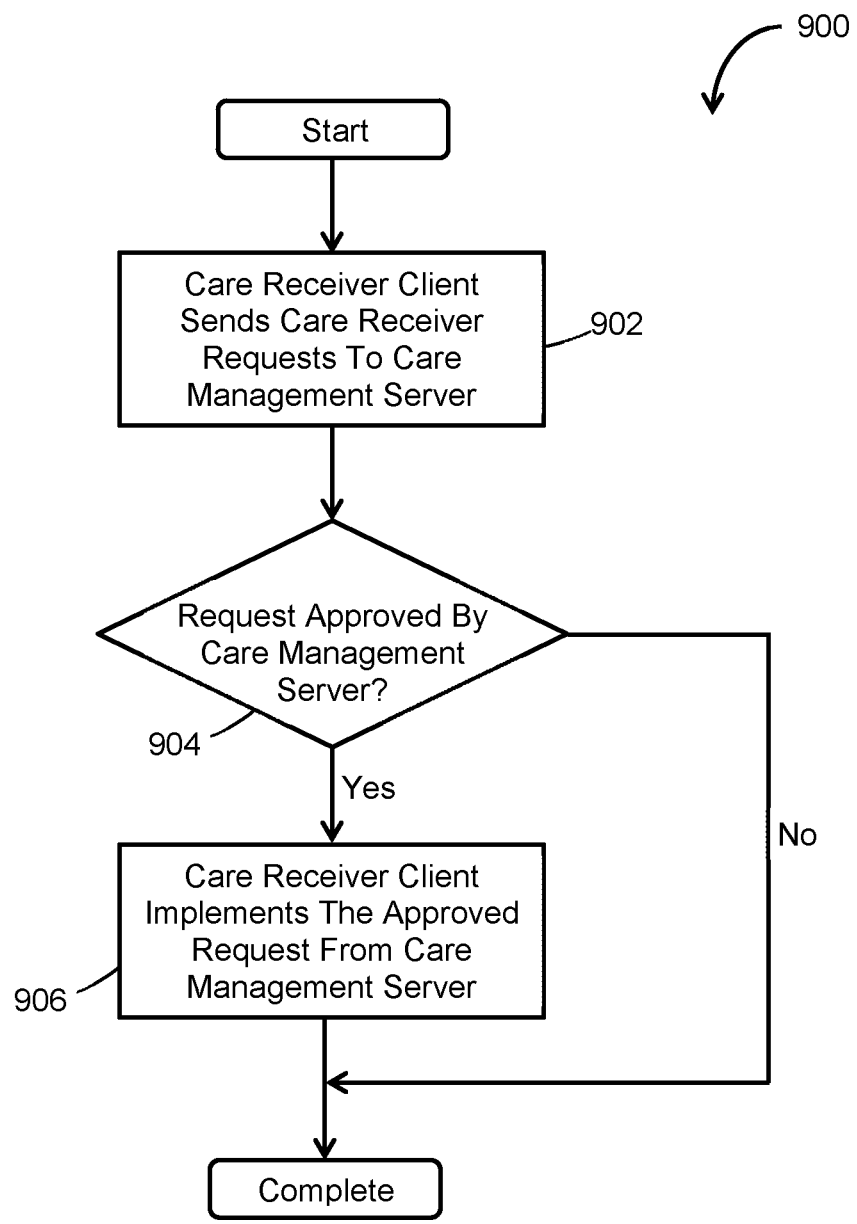
FIG. 9 is a flow chart illustrating a process in which a care management server fillers requests from a care receiver client in accordance with an embodiment of the invention.

In several embodiments, a care receiver client can request data from a care management server such as to browse the Internet, play games, teleconference, or to send or receive data. Requests can also include accessing email, social media, or the news. These requests are in turn moderated by the care management server. A flow chart illustrating a process for a care receiver client sending a request to a care management server, where the care receiver client implements the care receiver client request that is approved by a care management server in accordance with an embodiment of the invention is illustrated in FIG. 9. The process 900 begins with a care receiver client sending (902) a care receiver request to a care management server. After the care receiver request is sent, a decision (904) is made as to whether the request is approved by the care management server. If the request is approved by the care management server, then the care receiver client implements (906) the approved request from the care management server. If the request is not approved by the care management server, the process is complete and no action takes place.

Figure 10:
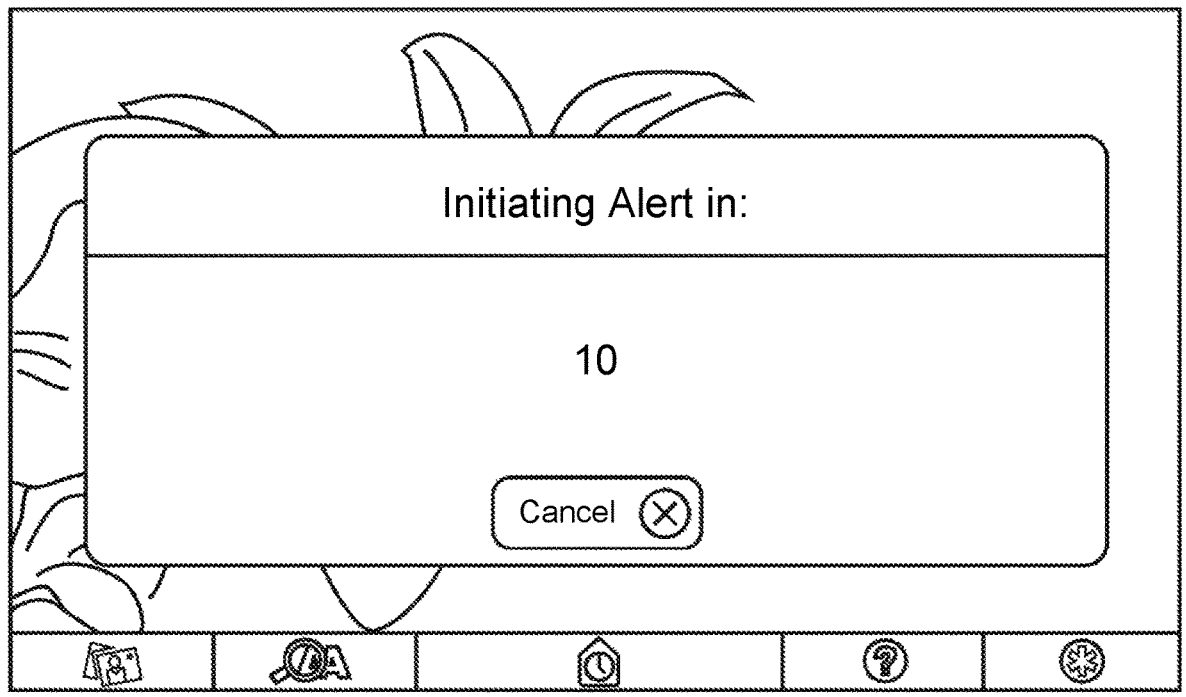
FIG. 10 illustrates a care receiver client alert screen in accordance with an embodiment of the invention.
Figure 11:
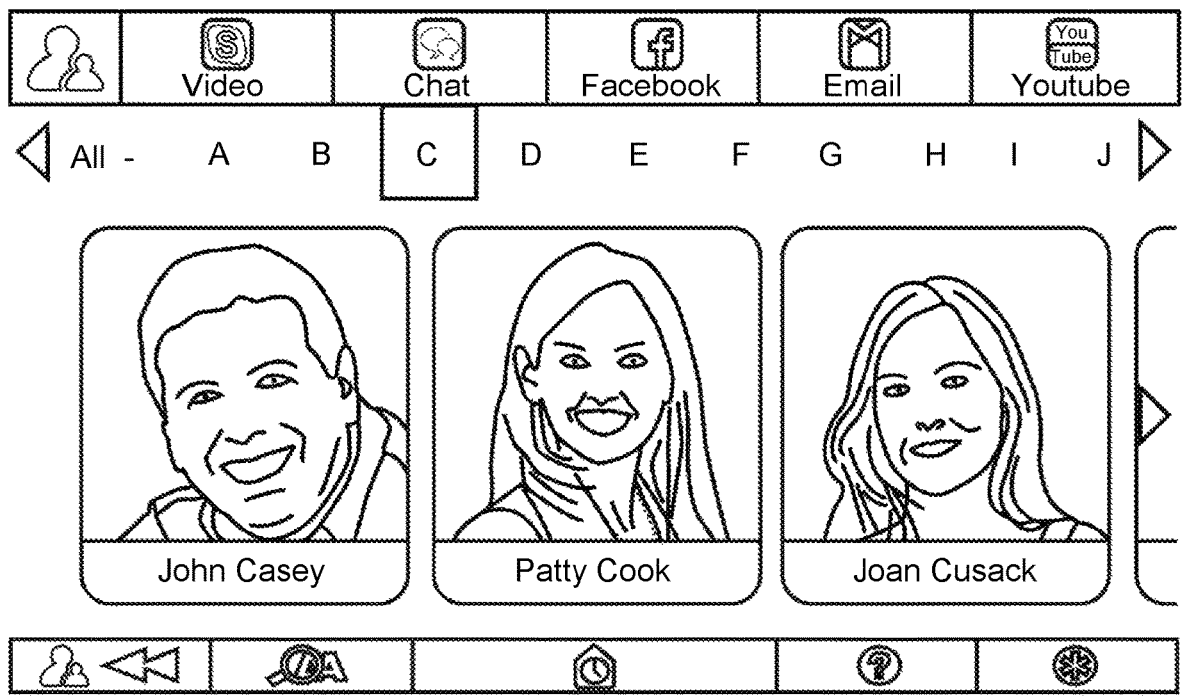
FIG. 11 illustrates a graphical contact list selection for video conferencing on a care receiver client user interface in accordance with an embodiment of the invention.
Figure 12:
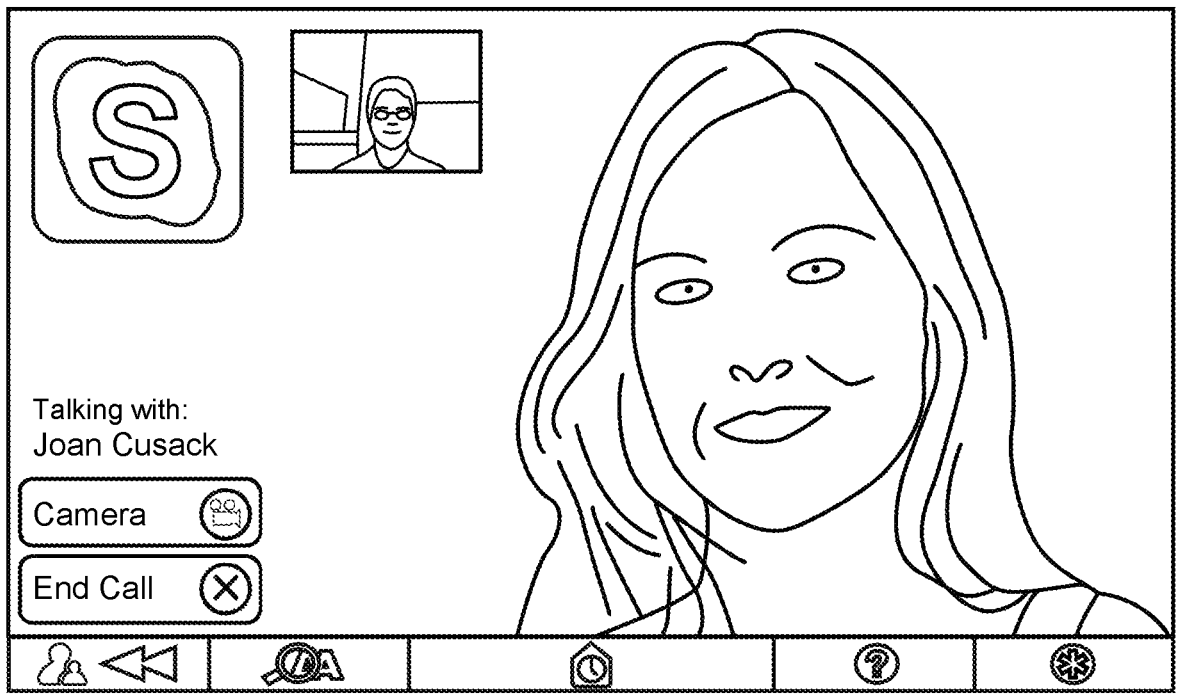
FIG. 12 illustrates a care receiver client user interface performing a videoconference in accordance with an embodiment of the invention.
Figure 13:
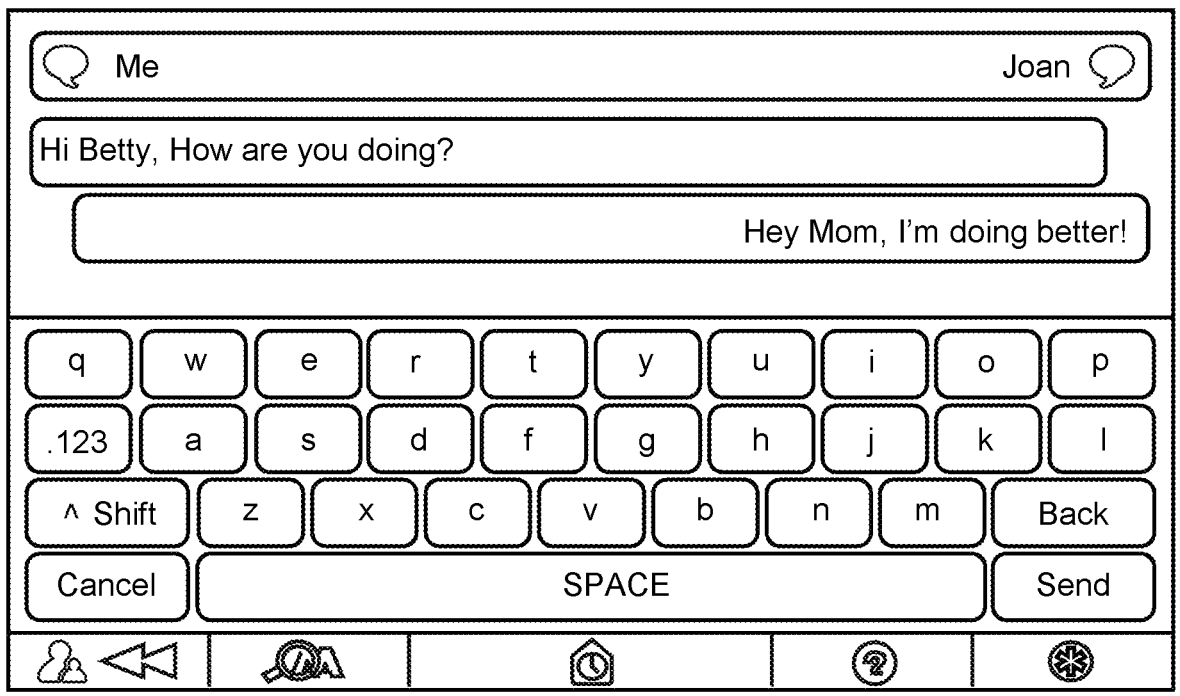
FIG. 13 illustrates messaging on a care receiver client user interface in accordance with an embodiment of the invention.

In various embodiments, a care receiver may want to communicate with a care provider such as in sending an alert or a call for help. An alert in accordance with an embodiment of the invention is illustrated in FIG. 10. In the illustrated embodiment, the alert can be initiated after an arbitrary amount of time, such as 10 seconds, to ensure that the care receiver actually meant to call for the alert. Similarly, a care receiver may seek to communicate with a care provider or a third party in another fashion. A user interface illustrating a video conference list in accordance with an embodiment of the invention is illustrated in FIG. 11. In the illustrated embodiment, pictures of the contacts are illustrated for ease of use for the care receiver. A videoconference performed via a care receiver client user interface in accordance with an embodiment of the invention is illustrated in FIG. 12. In the illustrated embodiment, a care receiver can control the videoconference such as by ending the call. Likewise, a care receiver can engage in text communication as well. Text communication from a care provider using a touch keypad on a care receiver client in accordance with an embodiment of the invention is illustrated in FIG. 13.

Figure 14:
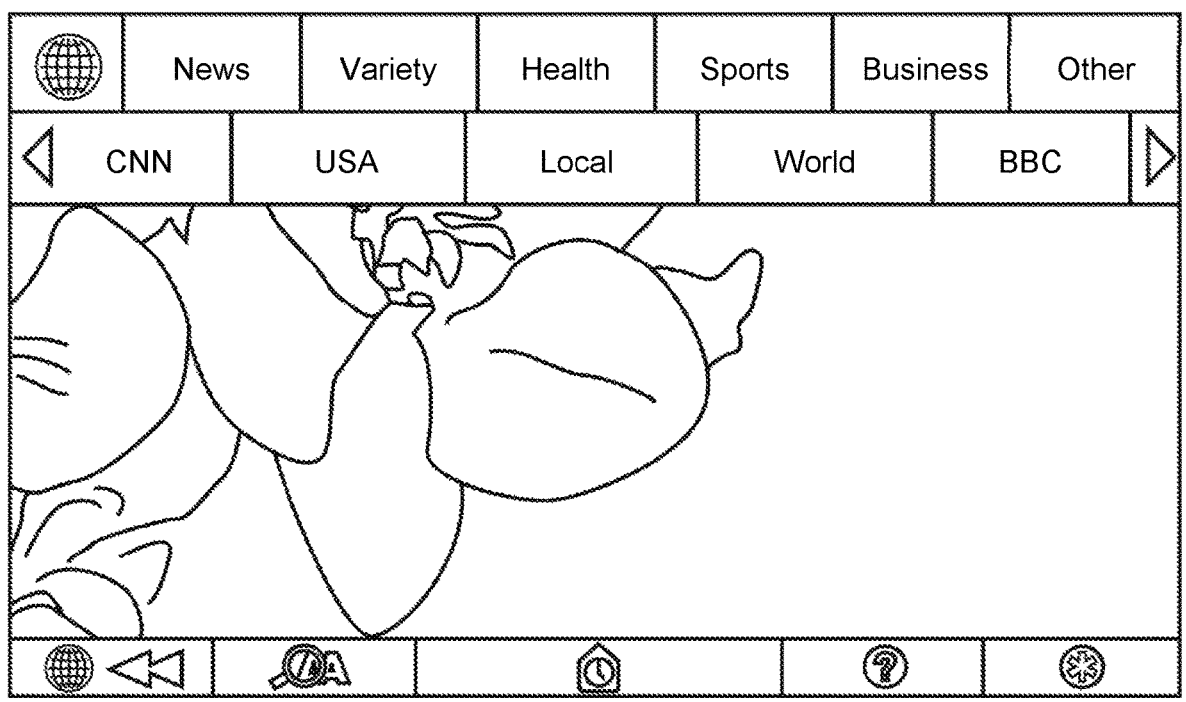
FIG. 14 illustrates selection of 3rd party programs on a care receiver client user interface in accordance with an embodiment of the invention.

A care receiver can also interact with third parties for information of interest to the care receiver, such as the news. A user interface for selecting news or other sources of data from a third party provider in accordance with an embodiment of the invention is illustrated in FIG. 14. In the illustrated embodiment, news or any other source of information of interest to the care receiver can be selected on the user interface. Thereby, the care receiver can manage information on a news service website.

Figure 15:
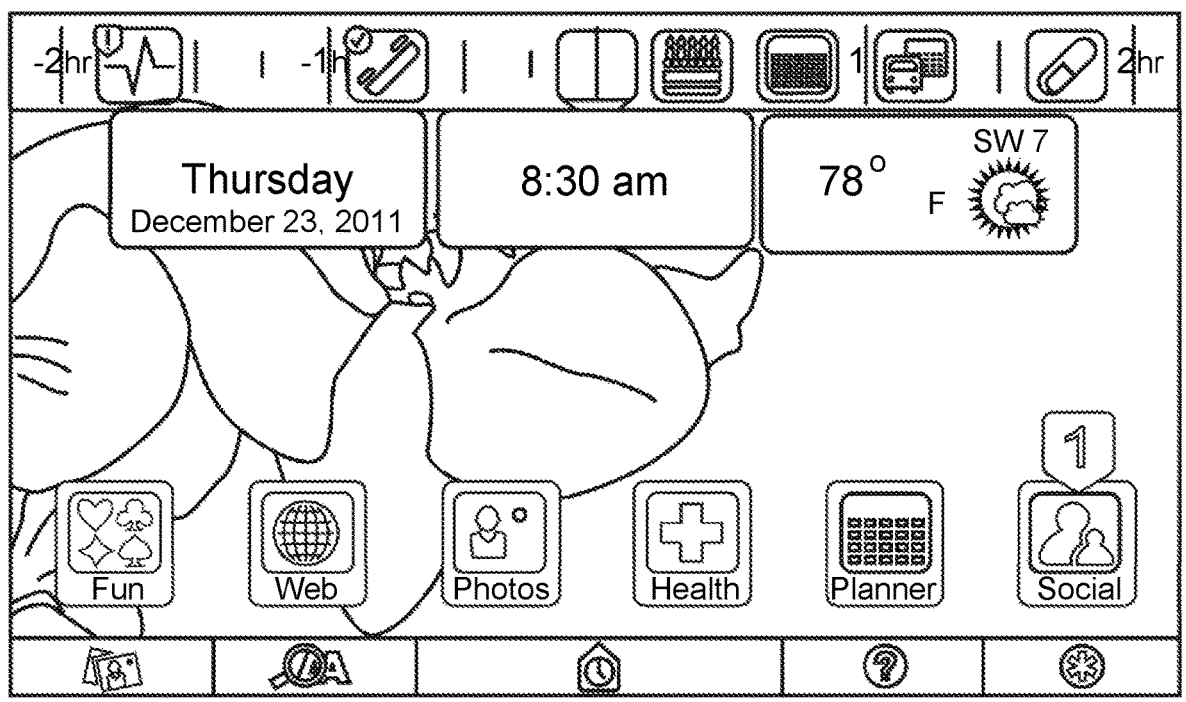
FIG. 15 illustrates a general graphical user interface on a care receiver client user interface in accordance with an embodiment of the invention.
Figure 16:
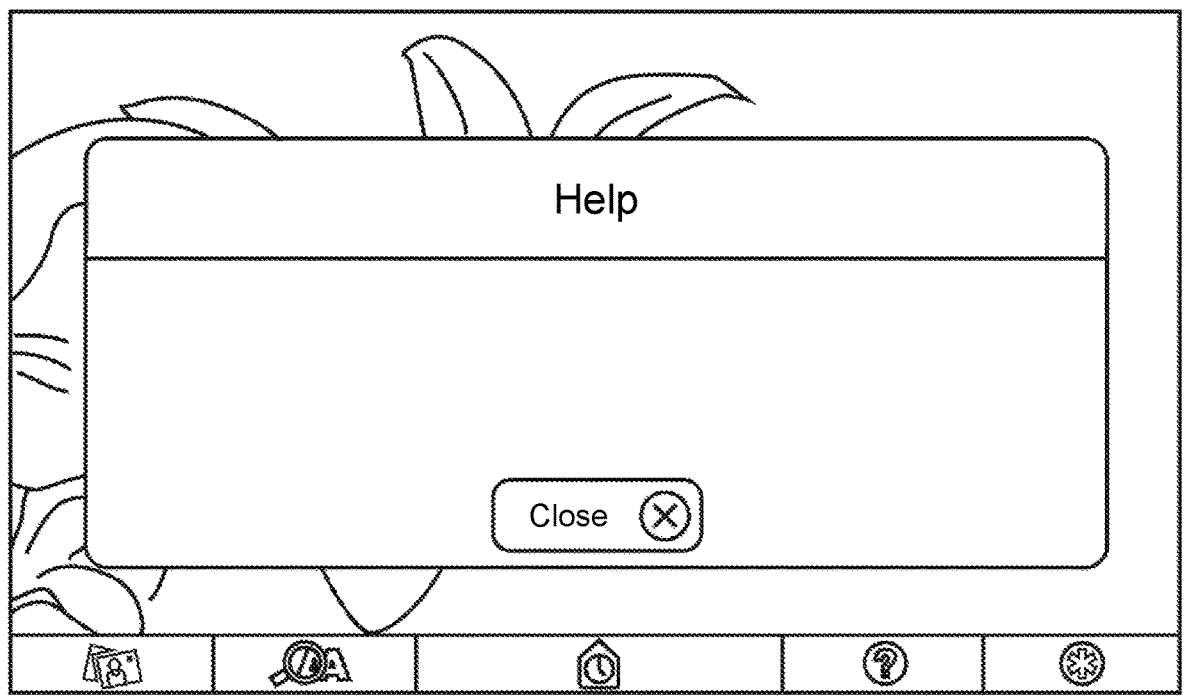
FIG. 16 illustrates a help tab on a care receiver client user interface in accordance with an embodiment of the invention.
Figure 17:
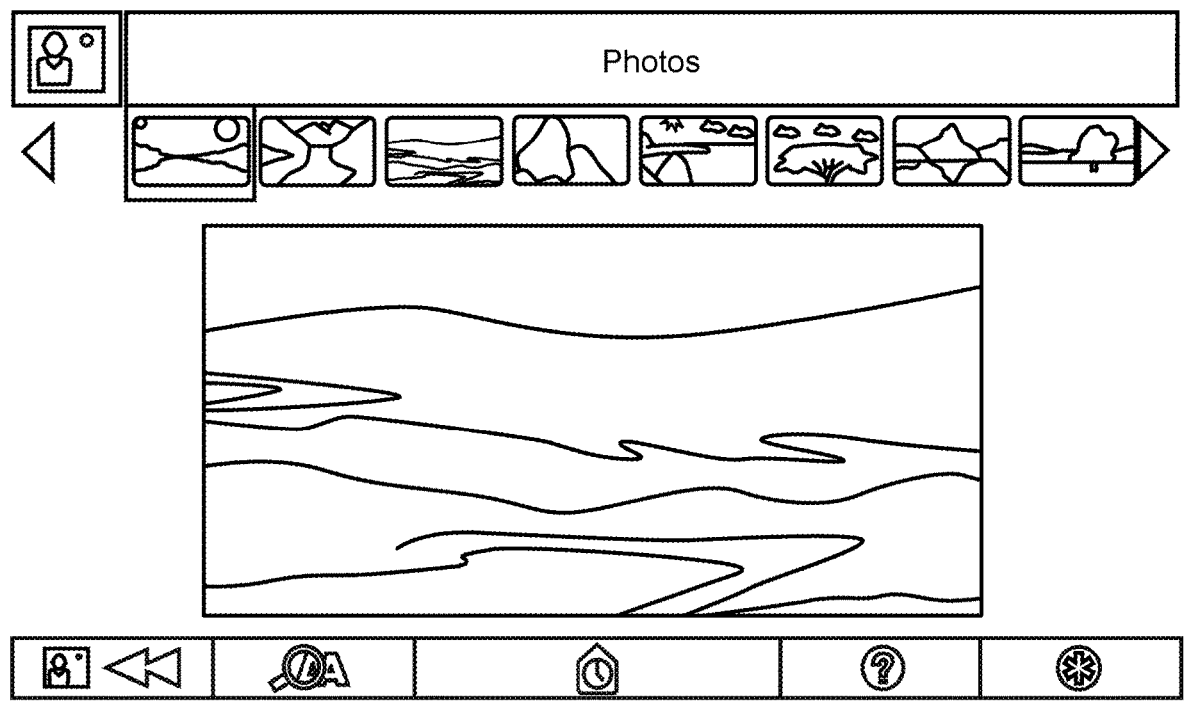
FIG. 17 illustrates a photo selection and viewing feature on a care receiver client user interface in accordance with an embodiment of the invention.
Figure 18:
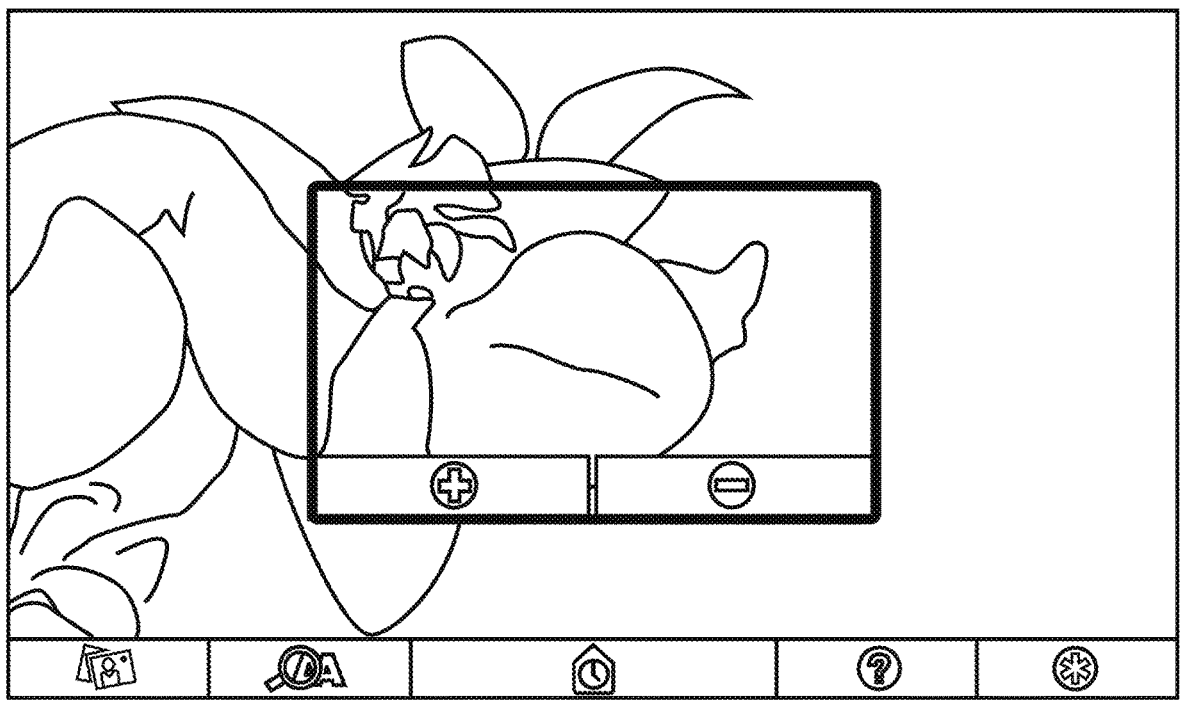
FIG. 18 illustrates a zooming feature on a care receiver client user interface in accordance with an embodiment of the invention.

In many embodiments, a care receiver navigates a user interface on a care receiver client to engage in an activity. The care receiver client can send a care receiver request to engage in that activity to a care management server. The care management server determines whether it approves the care receiver request. If the request is approved, the care receiver client implements the request for the activity and the activity proceeds. If not, then the process is complete and the activity does not proceed on the care receiver client. The activity can be a video conference, managing email or a social network, interacting with a webpage or browsing the news. The user interface can also include information generally of interest to the care receiver such as the time or weather. A user interface with information of general interest to a care receiver in accordance with an embodiment of the invention is illustrated in FIG. 15. Additionally, the user interface can also provide access to a help screen that allows for the care receiver to more easily navigate the user interface. A help screen on a care receiver client in accordance with an embodiment of the invention is illustrated in FIG. 16. A user interface can also include general features that are useful for a care receiver or that make a care receiver client more easy to use for the care receiver. Photo viewing on a care receiver client in accordance with an embodiment of the invention is illustrated in FIG. 17. In the illustrated embodiment, a number of photos can be viewed in thumbnails for ease of use. A zooming feature on a care receiver client in accordance with an embodiment of the invention is illustrated in FIG. 18. In the illustrated embodiment, a section of the care receiver client's graphical user interface can be selected and either zoomed in or out based upon the care receiver's instructions.

In some embodiments, care receiver client 112 (as described in connection with FIG. 1A) may include a television set. The television set may be configured to facilitate interactions between care providers and care recipients. The television set may be configured to provide interactive content to a care recipient. Interactive content may include one or more of videos, web sites, video chat, picture sharing, message sharing, concierge, menus, broadcast messages, surveys, community calendars, alerts, and/or other content. Interactive content may be sent to the care recipient from a care provider via care provider client 114 (as described in connection with FIG. 1).

Figure 19:
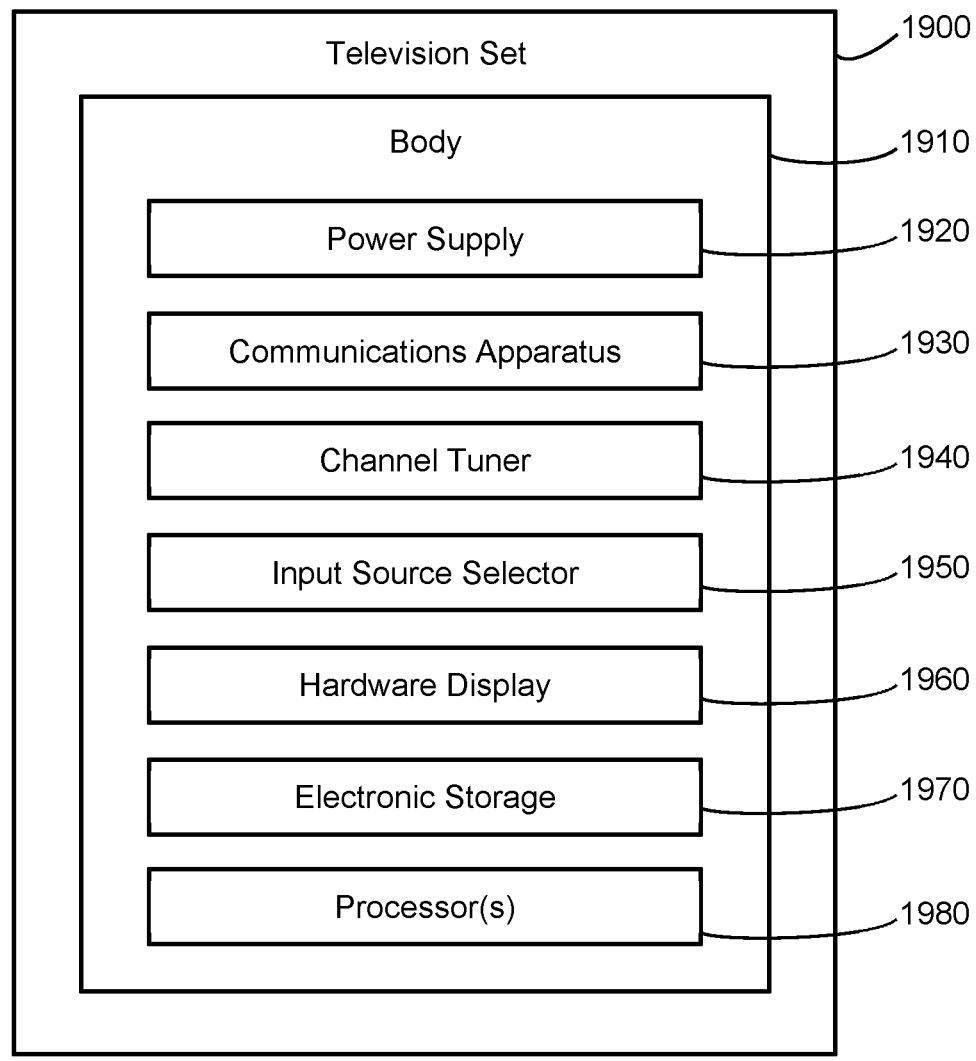
FIG. 19 illustrates a television set configured to facilitate third-party interactions without disturbing underlying content presentation, in accordance with some embodiments.

FIG. 19 illustrates a television set 1900 configured to facilitate third-party interactions without disturbing underlying content presentation, in accordance with some embodiments. Television set 1900 may include one or more of a body 1910, power supply 1920, communications apparatus 1930, channel tuner 1940, input source selector 1950, hardware display 1960, electronic storage 1970, one or more processor(s) 1980, and/or other components.

Body 1910 may be configured to carry one or more components of television set 1900. In some embodiments, body 1910 may be formed of plastic, wood, carbon fiber, and/or other materials. Body 1910 may include brackets, supports, picture tube, audio speakers, attachments, electronic elements, antennae, cable jacks, input jacks, output jacks, electronics for receiving remote control signals, and/or other components.

Power supply 1920 may be disposed within body 1910. Power supply 1920 may be configured to facilitate supply of electrical power to one or more components of television set 1900. By way of non-limiting example, power supply 1920 may include one or more of a battery, a capacitor, apparatus for receiving electrical power from an external source (e.g., a wall socket, solar panel), and/or other power supplies. In some implementations, power supply 1920 may be rechargeable.

Communications apparatus 1930 may be disposed within body 1910. Communications apparatus 1930 may be configured to receive television content. Communications apparatus 1930 may be configured to communicate with care management server 110 (as described in connection with FIG. 1A).

Channel tuner 1940, input source selector 1950, and/or other signal source components may be disposed within body 1910. Channel tuner 1940, input source selector 1950, and/or other signal source components may be configured to receive user selections conveying a change to a channel, an input source, and/or other signal source corresponding to specific television content. Channel tuner 1940, input source selector 1950, and/or other signal source components of television set 1900 may be configured to effectuate the change. By way of non-limiting example, hardware display 1960 may include one or more of a liquid-crystal display (LCD), a plasma display, a light-emitting diode (LED) display, an OLED (organic light-emitting diode) display, an LED-backlit LCD television, and/or other hardware displays.

Hardware display 1960 may be carried by body 1910. Hardware display 1960 may be configured to visually present the television content based on the channel, input source, and/or other signal source. In some embodiments, hardware display 1960 may be configured to provide an interface between television set 1900 and user(s) (e.g., care recipients, care providers, and/or other users) through which user(s) may provide information to and receive information from television set 1900. This may enable data, results, instructions and/or any other communicable items, collectively referred to as "information," to be communicated between the user(s) and one or more of processor(s) 1980, and/or electronic storage 1970.

In some embodiments, other communication devices, either hard-wired or wireless, may also be communicatively coupled with hardware display 1960. Examples of interface devices suitable for interaction with hardware display 1960 include a remote control, a keypad, a keyboard, a display screen, a touch screen, speakers, a microphone, an indicator light, an audible alarm, and/or other devices. In some embodiments, hardware display 1960 may be integrated with a removable storage interface provided by electronic storage 1970. In this example, information may be loaded into television set 1900 from removable storage (e.g., a smart card, a flash drive, a removable disk, etc.) that enables the user(s) to customize the implementation of television set 1900. Other exemplary input devices and techniques adapted for use with television set 1900 as hardware display 1960 include, but are not limited to, an RS-232 port, RF link, an IR link, modem (telephone, cable or other). In short, hardware display 1960 may include any technique for communicating information with television set 1900, in accordance with some embodiments.

Electronic storage 1970 may comprise non-transitory storage media that electronically stores information. The electronic storage media of electronic storage 1970 may include one or both of system storage that is provided integrally (e.g., substantially non-removable) with processor(s) 1980 and/or removable storage that is removably connectable to processor(s) 1980 via, for example, a port (e.g., a USB port, a firewire port, and/or other types of ports) or a drive (e.g., a disk drive and/or other types of drive). Electronic storage 1970 may include one or more of optically readable storage media (e.g., optical disks and/or other optically readable storage media), magnetically readable storage media (e.g., magnetic tape, magnetic hard drive, floppy drive, and/or other magnetically readable storage media), electrical charge-based storage media (e.g., EEPROM, RAM, and/or other electrical charge-based storage media), solid-state storage media (e.g., flash drive, and/or other solid-state storage media), and/or other electronically readable storage media.

Electronic storage 1970 may include one or more virtual storage resources (e.g., cloud storage, a virtual private network, and/or other virtual storage resources). Electronic storage 1970 may store software algorithms, information determined by processor(s) 1980, information received from processor(s) 1980, information received from communications apparatus 1930, information received from channel tuner 1940, information received from input source selector 1950, information received from hardware display 1960, information received from care management server 110, information associated with machine-readable instructions, and/or other information that enables television set 1900 to function as described herein.

Processor(s) 1980 may be configured to provide information processing capabilities in television set 1900 as a whole. As such, processor(s) 1980 may include one or more of a digital processor, an analog processor, a digital circuit designed to process information, an analog circuit designed to process information, a state machine, and/or other mechanisms for electronically processing information. Although processor(s) 1980 is shown in FIG. 19 as a single entity, this is for illustrative purposes only. In some embodiments, processor(s) 1980 may include a plurality of processing units. These processing units may be physically located within the same device, or processor(s) 1980 may represent processing functionality of a plurality of devices operating in coordination.

In some embodiments, processor(s) 1980 may be configured to facilitate interactivity between television set 1900 and care recipients as an embedded feature of processor(s) 1980, television set 1900, and/or other components. An interaction between television set 1900 and the care recipient may be initiated without processor(s) 1980, television set 1900, and/or other components receiving a user selection of an application from among a set of available applications visually presented via the given television sets.

Processor(s) 1980 may be configured to execute machine-readable instructions by software; hardware; firmware; some combination of software, hardware, and/or firmware; and/or other mechanisms for configuring processing capabilities on processor(s) 1980. As used herein, the term "machine-readable instructions" may refer to any component or set of components that perform the functionality attributed to the machine-readable instruction component. This may include one or more physical processors during execution of processor readable instructions, the processor readable instructions, circuitry, hardware, storage media, or any other components.

Processor(s) 1980 may be configured by machine-readable instructions to perform a method for facilitating third-party interactions via hardware display 1960 without disturbing the television content presentation. The method may include effectuating visual presentation via hardware display 1960 of a user interface for receiving care management instructions. The user interface may be laid over the television content such that the user interface may be presented regardless of the selected channel or input source. The user interface may be laid over the television content such that, in a first mode of operation, the presentation of the television content may be not paused when the user interface may be presented.

The care management server 110 may be configured to receive information related to the status of a care recipient using automated user interface interactions via communications apparatus 1930. The care management server 110 may be configured to send automatically generated notifications to communications apparatus 1930. Notifications may be based upon the analysis of the care management database 108 (as described in connection with FIG. 1). The care management server 110 may be configured to receive data concerning the status of a care recipient via communications apparatus 1930. The care management server 110 may be configured to send notifications to communications apparatus 1930 based upon the analysis of the care management database.

Communications apparatus 1930 may be configured to access content servers. The care management server 110 may be configured to restrict the content servers that communications apparatus 1930 can access. Communications apparatus 1930 may be configured to display a game user interface via hardware display 1960. Communications apparatus 1930 may be configured to record game performance. Communications apparatus 1930 may be configured to send game performance data to the care management server 110. The care management server 110 may be configured to receive game performance data from communications apparatus 1930. The care management server 110 may be configured to store the game performance data in the care management database. The care management server 110 may be configured to analyze the game performance data. The care management server 110 may be configured to send a notification to the care provider client 114. The care management server 110 may be configured to send a notification to the care provider client 114 in response to the analysis detecting a decline in game performance. The game user interface may include one or more cognitive skills exercise games and/or other tools. The cognitive skills exercise games and/or tools may be configured to facilitate cognitive interaction with the care recipient.

Communications apparatus 1930 may be configured to transmit data concerning the status of a care recipient via the care receiver sensor 102 (as described in connection with FIG. 1). The care management server 110 may be configured to communicate with communications apparatus 1930, care receiver sensor 102, and/or the care provider client 114 via the Internet. Communications apparatus 1930 and/or care receiver sensor 102 may be configured to connect to the Internet. The care management server 110 may be configured to transmit data concerning the status of a care recipient via communications apparatus 1930 and/or the care receiver sensor 102. The care management server 110 may be configured to update the configuration settings of communications apparatus 1930 and/or the care receiver sensor 102 based upon the analysis of the data concerning the status of the care recipient in the care management database 108. The care provider client 114, communications apparatus 1930, and/or the care receiver sensor 102 may be configured to intermittently synchronize with the care management server 110. The care management server 110 may transmit scheduling data to communications apparatus 1930.

The care management server 110 may be configured to analyze the data within the care management database 108 to generate a timeline of upcoming notifications. The care management server 110 may be configured to send the timeline of upcoming notifications to communications apparatus 1930 and/or the care provider client 114. Communications apparatus 1930 may display the timeline of upcoming notifications via the user interface. The care management server 110 may be configured to analyze the data within the care management database 108 and send escalated notifications based upon the care management instructions stored in the care management database 108 to communications apparatus 1930 and/or the care provider client 114. Communications apparatus 1930 may display the escalated notifications via the user interface.

In some embodiments, television set 1900 may be configured to deliver incoming media content on top of the existing television content currently being displayed or broadcast. Incoming media content may include one or more of videos, web sites, cloud based content, and/or other content. Incoming media content may be delivered to television set 1900 in one or more modes. By way of non-limiting example, a care recipient may receive a text notification displayed over the standard television programming the care recipient is watching.

In the first mode of operation, the user interface may be laid over a portion of the television content such that the user interface may be presented regardless of the selected channel or input source. In the first mode of operation, the presentation of the television audio and video content may be not paused when the user interface is presented via hardware display 1960. In the first mode of operation, the user interface presented may include one or more of a message, an alert, a notification, multimedia, and/or other content. In some embodiments, the user interface may present the message, the notification, alert, multimedia, and/or other content for a duration in a range between about five seconds and about 30 seconds, inclusive (e.g., ten seconds, fifteen seconds, twenty seconds, twenty-five seconds, and/or other durations). As a non-limiting example, a care recipient may be watching TV normally and the user interface displaying text and/or media may cover a portion of the television content. The covered portion may be the top right portion of the television content and/or other areas. The user interface may be presented via a drop down action and/or via other types of action. The user interface may display a notice to the care recipient. The notice may inform the care recipient of having received a new picture, a new message, and/or other social engagement items being delivered. In some embodiments, the visual content and/or audio content may remain unchanged.

In some embodiments, the user interface may be laid over the television content such that in a second mode of operation, the presentation of the television audio content is not paused when the user interface is presented via hardware display 1960. In a second mode of operation, the user interface presented may include one or more of a message, an alert, a notification, a reminder, multimedia, video, and/or other visual content. The presentation of the television video content may resume responsive to completion of the second mode of operation. As a non-limiting example, a care recipient may be watching TV normally at which time the user interface displaying text and/or media may cover a portion of or all of a visual area of the television or other care receiver client via a drop down or other action. In some embodiments, the audio content may continue unchanged. Presence of the user interface may occur responsive to the care recipient receiving a reminder, a new picture, a new message, and/or other social engagement items being delivered.

In some embodiments, the user interface may be laid over the television content such that in a third mode of operation, the presentation of the television content is interrupted when the user interface is presented via hardware display 1960. In the third mode of operation, the user interface presented may include multimedia, video content, website, network content, two-way communication via real-time audio and/or video, video chat, voice call, and/or other media content. The presentation of the television audio and video content may resume responsive to completion of the third mode of operation. As a non-limiting example, a care recipient may be watching TV normally and the user interface displaying text or media may cover a portion of or all of a visual area of the television or other care receiver client via a drop down and/or other action as well as stop, pause, and/or delay the audio content. Presence of the user interface may occur responsive to the care recipient receiving a reminder, a new picture, a new message, or other social engagement items being delivered. In some embodiments, the audio content may remain unchanged.

In some embodiments, the user interface and/or communications apparatus 1930 may be configured to facilitate interaction with a graphical user interface (GUI), application program (app), television set software, web application (web app), mobile app, application software, and/or other content.

In some embodiments, the care management server 110 may be configured to receive audio and/or video information from the care recipient via communications apparatus 1930, the communications port, a personal computing device, the user interface, telephone, app, web app, mobile app, communications network, and/or other sources. The care management server 110 may be configured to record the audio and/or video information and/or store the audio or video information in the care management database. The audio or video information from the care recipient may be narrative dictated by the care recipient. The narrative may be a care recipient's life stories.

In some embodiments, the interactivity between television sets and third-party interactions may be facilitated responsive to the given television set receiving a user selection via channel tuner 1940, input source selector 1950, communications apparatus 1930, application software, and/or other component.

In some embodiments, the interactivity between television sets and third-party interactions may be an embedded feature of television set 1900. An interaction between a given television set and a given third-party interaction may be initiated without the given television set receiving a user selection. An interaction between a given television set and a given third-party interaction may be initiated by the given television set receiving a user selection of an application from among a set of available applications visually presented via the given television sets.

In another embodiment, care receiver client 112 (as described in connection with FIG. 1A) may be a device such as a set-top-box (STB), a cable STB, a satellite STB, a Roku STB, an Apple TV STB, a HD Antenna, and/or other device configured to provide media content. The device may be configured to facilitate interactions between care providers and care recipients. The device may be configured to provide interactive content as described above to a care recipient.

Figure 20:
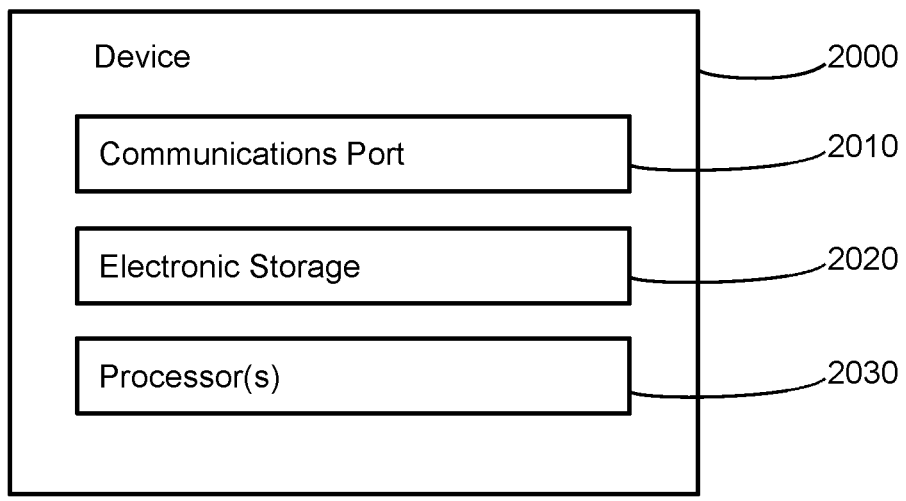
FIG. 20 illustrates a device configured to communicatively couple with a television set to facilitate third-party interactions without disturbing underlying content presentation by the television set, in accordance with some embodiments.

FIG. 20 illustrates a device 2000 configured to communicatively couple with a television set to facilitate third-party interactions without disturbing underlying content presentation by the television set, in accordance with some embodiments. Device 2000 may be configured to communicatively couple with a television set the same as or similar to television set 1900 (as described in connection with FIG. 19). Device 2000 may include a communications port 2010, electronic storage 2020, one or more hardware processors 2030, and/or other components.

Communications port 2010 may be configured to facilitate a communicative coupling with the television set. Communicative coupling may be via a hard-wired connection, wireless connection, and/or other connection.

Electronic storage 2020 may comprise non-transitory storage media that electronically stores information. The electronic storage media of electronic storage 2020 may include one or both of system storage that is provided integrally (e.g., substantially non-removable) with processor(s) 2030 and/or removable storage that is removably connectable to processor(s) 2030 via, for example, a port (e.g., a USB port, a firewire port, and/or other types of ports) or a drive (e.g., a disk drive and/or other types of drive). Electronic storage 2020 may include one or more of optically readable storage media (e.g., optical disks and/or other optically readable storage media), magnetically readable storage media (e.g., magnetic tape, magnetic hard drive, floppy drive, and/or other magnetically readable storage media), electrical charge-based storage media (e.g., EEPROM, RAM, and/or other electrical charge-based storage media), solid-state storage media (e.g., flash drive, and/or other solid-state storage media), and/or other electronically readable storage media.

Electronic storage 2020 may include one or more virtual storage resources (e.g., cloud storage, a virtual private network, and/or other virtual storage resources). Electronic storage 2020 may store software algorithms, information determined by processor(s) 2030, information received from processor(s) 2030, information received from communications port 2010, information received from care management server 110, information associated with machine-readable instructions, and/or other information that enables device 2000 to function as described herein.

Device 2000 may include one or more hardware processors 2030. Processor(s) 2030 may be configured to provide information processing capabilities in device 2000 as a whole. As such, processor(s) 2030 may include one or more of a digital processor, an analog processor, a digital circuit designed to process information, an analog circuit designed to process information, a state machine, and/or other mechanisms for electronically processing information. Although processor(s) 2030 is shown in FIG. 20 as a single entity, this is for illustrative purposes only. In some embodiments, processor(s) 2030 may include a plurality of processing units. These processing units may be physically located within the same device, or processor(s) 2030 may represent processing functionality of a plurality of devices operating in coordination. Processor(s) 2030 may be configured by the machine-readable instructions to perform a method for facilitating third-party interactions via a hardware display the same as or similar to hardware display 1960 (as described in connection with FIG. 19), without disturbing the television content presentation.

In some embodiments, interactivity between television sets and third-party interactions may be an embedded feature of device 2000. An interaction between a given television set and a given third-party interaction may be initiated without device 2000 and/or the given television set receiving a user selection. In other embodiments, an interaction between a given television set and a given third-party interaction may be initiated by device 2000 and/or the given television set receiving a user selection of an application from among a set of available applications visually presented via the given television set. As a non-limiting example, device 2000 may be connected with a care recipient's television set. The care recipient may be watching TV normally via the television set. Responsive to the care recipient receiving a reminder, a new picture, a new message, a call, a chat, and/or other social engagement items being delivered, the user interface displaying text and/or media may cover a portion of or all of a visual area of the television set and/or pause the previously presented audio and/or video content being displayed by the television set.

In some embodiments, device 2000 may be configured to communicatively couple with a television set via one or more of HDMI, HDMI-in, HDMI-out, optical audio, composite video/audio, RCA composite, optical cable, and/or other wired or wireless connectivity. In some embodiments, device 2000 may be configured to communicatively couple with a communication module other than a television set such as an eye-glass, video-headset, personal computing device, and/or other devices.

In some embodiments, device 2000 may be a set-top box (STB), digital media player set-top box, set-top unit, information appliance device, cable converter box, digital television adapter, closed captioning box, IPTV receiver, professional set-top box, hybrid box, UHF converter, and/or other information appliance device. Device 2000 may be configured to overlay received content as described above in connection with the systems and methods of television set 1900.

In some embodiments, device 2000 may include a TV-tuner. Device 2000 may be configured to receive a broadcasting signal from one or more of cable television, satellite television, over-the-air television, Internet Protocol television (IPTV), an Ethernet cable, a satellite dish, a coaxial cable, a telephone line, a DSL connection, broadband over power lines (BPL), a VHF antenna, a UHF antenna, cable STB, satellite STB, Roku STB, Apple TV STB, HD Antenna, and/or other devices configured to provide media content.

A system, the same as or similar to care management system 100 (as described in connection with FIG. 1A), may be configured for facilitating interactions between television sets the same as or similar to television set 1900 (as described in connection with FIG. 19), and personal computing devices, the same as or similar to care provider client 114 (as described in connection with FIG. 1A). The system may comprise one or more physical servers, including a care management server 110 the same as or similar to care management server 110 (as described in connection with FIG. 1A), configured to be communicatively coupled with one or more television sets including a first television set.

The system may comprise one or more personal computing devices including a first personal computing device. The care management server 110 may include a non-transitory storage medium having a care management database the same as or similar to care management database 108 (as described in connection with FIG. 1A) and machine-readable instructions embodied thereon. The care management server 110 may include one or more hardware processors configured by the machine-readable instructions to receive first care management instructions and/or data concerning the status of a care recipient associated with the first television set. The first care management instructions may be received via a first user interface visually presented via a first hardware display of the first television set. The first user interface may be laid over television content such that the first user interface is presented regardless of a selected channel or input source.

In a first mode of operation, the presentation of the television content is not paused when the first user interface is presented by the first television set. The care management server 110 may be configured to receive second care management instructions via a second user interface visually presented via a second hardware display of the first personal computing device. The second user interface may be presented via an app executed by the first personal computing device. The care management server 110 may be configured to store the first care management instructions, the data concerning the status of the care recipient, second care management instructions, and/or other information in the care management database.

The care management server 110 may be configured to analyze the care management database in accordance with the care management instructions. The care management server 110 may be configured to provide notifications to the first television set and/or the personal computing devices based upon the analysis of the care management database. The care management server 110 may be configured to receive data concerning the status of the care recipient using automated user interface interactions via a telephone. The care management server 110 may be configured to send automatically generated notifications to the telephone based upon the analysis of the care management database. The care management server 110 may be configured to receive data concerning the status of the care recipient via the first user interface. The care management server 110 may be configured to send notifications to the second user interface based upon the analysis of the care management database.

One or both of the first user interface and the second user interface may be configured to access content servers. The care management server 110 may be configured to restrict the content servers that one or both of the first user interface and the second user interface can access. The first user interface may be configured to display a game user interface, record game performance, send game performance data to the care management server 110, and/or other activities. The care management server 110 may be configured to receive game performance data from the first user interface and store the game performance data in the care management database, analyze the game performance data, send a notification to the second user interface in response to the analysis detecting a decline in game performance, and/or other responses.

The care management server 110 may be configured to communicate with one or more of the first user interface, the care receiver sensor, a second user interface, and/or other devices via the Internet. The first user interface and/or the care receiver sensor may be configured to connect to the Internet. The care management server 110 may be configured to receive data concerning the status of the care recipient via one or more of the first user interface and/or the care receiver sensor. The care management server 110 may be configured to update the configuration settings of the first user interface and the care receiver sensor based upon the analysis of the data concerning the status of the care recipient in the care management database. The first user interface, the second user interface, and/or the care receiver sensor may be configured to intermittently synchronize with the care management server 110. The care management server 110 may receive scheduling data from the first user interface. The care management server 110 may be configured to send the timeline of upcoming notifications to at least one of the first user interface and the second user interface, which displays a timeline of upcoming notifications. The care management server 110 may be configured to analyze the data within the care management database and send escalated notifications based upon the first care management instructions and/or second care management instructions stored in the care management database.

In some embodiments, in the first mode of operation, the first user interface is laid over a portion of the television content such that the first user interface is presented regardless of the selected channel or input source and such that the presentation of the television audio and video content is not paused when the first user interface is presented by the first television set. The first user interface presented by the first television set in the first mode of operation may include a message, a notification, multimedia, and/or other content. The first user interface may present the message, the notification, the multimedia, and/or other content for a duration in a range between about five seconds and about 30 seconds, inclusive (e.g., ten seconds, fifteen seconds, twenty seconds, twenty-five seconds, and/or other durations).

In some embodiments, the first user interface may be laid over the television content such that, in a second mode of operation, the presentation of the television audio content is not paused when the first user interface is presented by the first television set. The first user interface presented by the first television set in the second mode of operation may include a message, a notification, a reminder, multimedia, video, and/or other visual content. The presentation of the television video content may resume responsive to completion of the second mode of operation.

In some embodiments, the first user interface may be laid over the television content such that, in a third mode of operation, the presentation of the television content is interrupted when the first user interface is presented by the first television set. The first user interface presented by the first television set in the third mode of operation may include multimedia, video content, website, network content, two-way communication via real-time audio or video, video chat, voice call, and/or other media content. The presentation of the television audio and video content may resume responsive to completion of the third mode of operation.

In some embodiments, the first user interface and/or the second user interface may be configured to facilitate interaction with a graphical user interface (GUI), application program (app), systems software, web application (web app), mobile app, application software, and/or other programs.

In some embodiments, the care management server 110 may be configured to receive audio and/or video information from the care recipient via the personal computing device, the first user interface, telephone, app, web app, mobile app, communications network, and/or other component. The care management server 110 may be configured to record the audio and/or video information and store the audio and/or video information in the care management database.

In some embodiments, the system may be configured to facilitate interactions between television sets and personal computing devices responsive to a user selection initiating the system via a channel tuner, input source selector, application software, and/or other component.

In some embodiments, interactivity between television sets and personal computing devices may be an embedded feature of the television sets. An interaction between a given television set and a given personal computing device may be initiated without the given television set receiving a user selection of an application from among a set of available applications visually presented via the given television sets.

Figure 21:
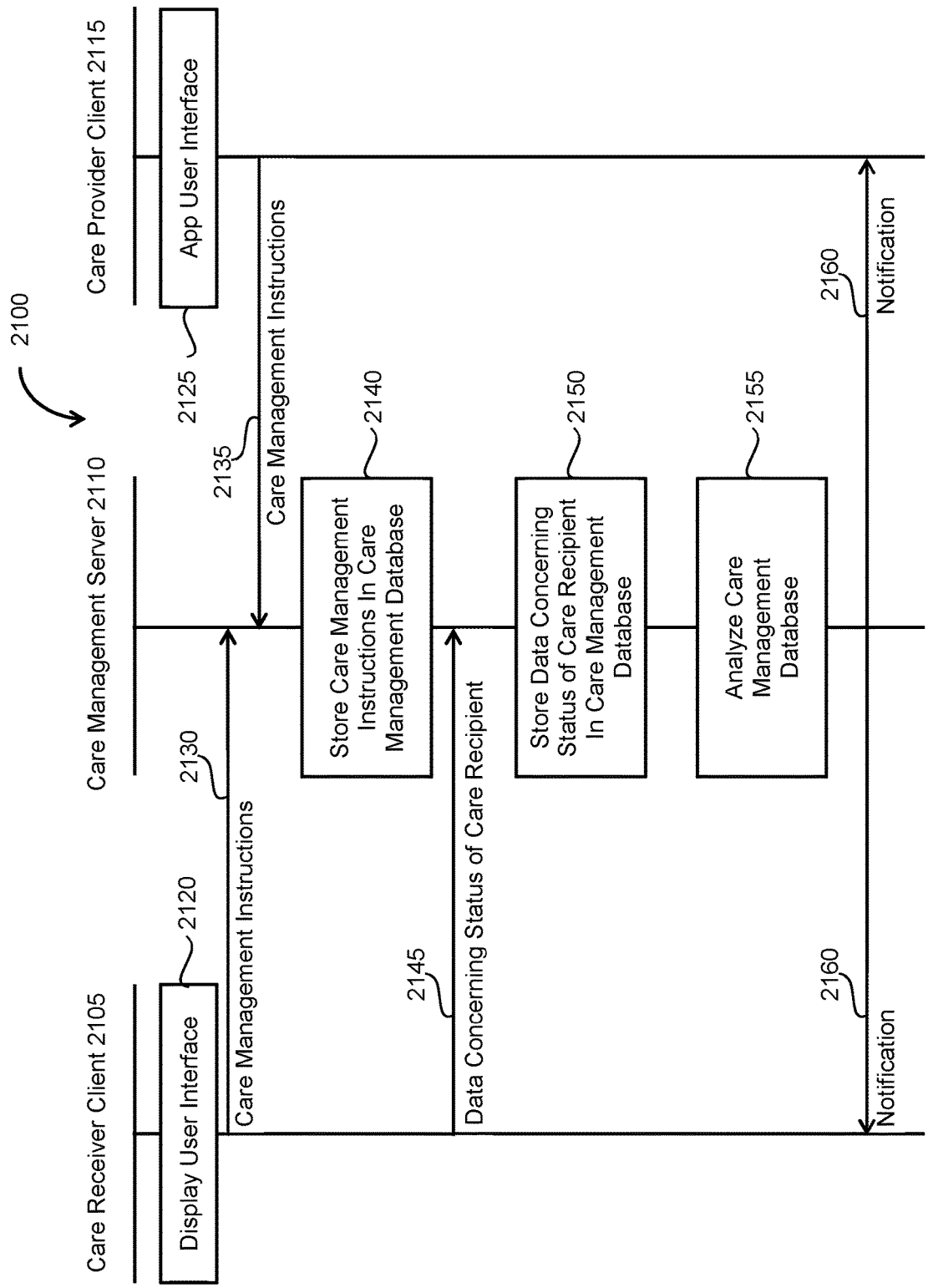
FIG. 21 illustrates a method for facilitating interactions between care receiver clients and care provider clients, in accordance with some embodiments.

FIG. 21 illustrates a method 2100 for facilitating interactions between care receiver clients 2105 and care provider clients 2115, in accordance with some embodiments. In some embodiments, care receiver clients 2105 may include television sets. In some embodiments, care provider clients 2015 may include personal computing devices. The method 2100 may be performed by one or more physical servers including a care management server 2110. Care management server 2110 may be configured to be communicatively coupled with one or more care receiver clients 2105, including a first television set, and one or more care provider clients 2115, including a first personal computing device.

In some embodiments, one or more operations of method 2100 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 2100 in response to instructions stored electronically on an electronic storage medium. The one or more processing devices may include one or more devices configured through hardware, firmware, and/or software to be specifically designed for execution of one or more of the operations of method 2100.

At an operation 2120, effectuate visual presentation via the hardware display of a first user interface for receiving care management instructions. In some embodiments, The user interface may be laid over the television content such that the user interface may be presented regardless of the selected channel or input source and such that, in a first mode of operation, the presentation of the television content may be not paused when the user interface is presented. Operation 2120 may be performed by one or more hardware processors configured to execute a machine-readable instruction component that is the same as or similar to television set 1900 (as described in connection with FIG. 19), in accordance with one or more embodiments.

At an operation 2125, effectuate visual presentation via a second user interface visually presented via a second hardware display of the first personal computing device. The second user interface may be presented via an app executed by the first personal computing device. Operation 2125 may be performed by one or more hardware processors configured to execute a machine-readable instruction component that is the same as or similar to care provider client 114 (as described in connection with FIG. 1A), in accordance with one or more embodiments.

At an operation 2130, receive first care management instructions. Operation 2130 may be performed by one or more hardware processors configured to execute a machine-readable instruction component that is the same as or similar to television set 1900 (as described in connection with FIG. 19), in accordance with one or more embodiments.

At an operation 2135, receive second care management instructions via a second user interface visually presented via a second hardware display of the first personal computing device. The second user interface may be presented via an app executed by the first personal computing device. Operation 2135 may be performed by one or more hardware processors configured to execute a machine-readable instruction component that is the same as or similar to care provider client 114 (as described in connection with FIG. 1A), in accordance with one or more embodiments.

At an operation 2140, store the first care management instructions and second care management instructions in the care management database. Operation 2140 may be performed by one or more hardware processors configured to execute a machine-readable instruction component that is the same as or similar to care management server 110 (as described in connection with FIG. 1A), in accordance with one or more embodiments.

At an operation 2145, receive data concerning the status of a care recipient associated with the first television set via a first user interface visually presented via a first hardware display of the first television set. Operation 2145 may be performed by one or more hardware processors configured to execute a machine-readable instruction component that is the same as or similar to television set 1900 (as described in connection with FIG. 19), in accordance with one or more embodiments.

At an operation 2150, store the data concerning the status of the care recipient. Operation 2150 may be performed by one or more hardware processors configured to execute a machine-readable instruction component that is the same as or similar to care management server 110 (as described in connection with FIG. 1A), in accordance with one or more embodiments.

At an operation 2155, analyze the care management database in accordance with the care management instructions. Operation 2155 may be performed by one or more hardware processors configured to execute a machine-readable instruction component that is the same as or similar to care management server 110 (as described in connection with FIG. 1A), in accordance with one or more embodiments.

At an operation 2160, provide notifications to one or both of the first television set or the personal computing devices based upon the analysis of the care management database. Operation 2160 may be performed by one or more hardware processors configured to execute a machine-readable instruction component that is the same as or similar to care management server 110 (as described in connection with FIG. 1A), in accordance with one or more embodiments.

While the above description contains many specific embodiments, these should not be construed as limitations on the scope of the present disclosure, but rather as an example of some embodiments thereof.

What is claimed is:

1. A system configured for facilitating interactions between television sets and personal computing devices, the system comprising:
one or more physical servers, including a care management server, configured to be communicatively coupled with one or more television sets including a first television set and one or more personal computing devices including a first personal computing device, the care management server comprising a non-transitory storage medium having a care management database and machine-readable instructions embodied thereon, the care management server further comprising one or more hardware processors configured by the machine-readable instructions to:
receive first care management instructions and data concerning the status of a care recipient associated with the first television set via a first user interface visually presented via a first hardware display of the first television set, the first user interface being laid over television content such that the first user interface is presented regardless of a selected channel or input source and such that, in a first mode of operation, the presentation of the television content is not paused when the first user interface is presented by the first television set;
receive second care management instructions via a second user interface visually presented via a second hardware display of the first personal computing device, the second user interface being presented via an app executed by the first personal computing device;
store the first care management instructions, the data concerning the status of the care recipient, and second care management instructions in the care management database;
analyze the care management database in accordance with the first and second care management instructions;
provide notifications to one or both of the first television set or the personal computing devices based upon the analysis of the care management database;
wherein the care management server is further configured to: receive data concerning the status of the care recipient via the first user interface; and send notifications to the second user interface based upon the analysis of the care management database; and
wherein: one or both of the first user interface and the second user interface is configured to access content servers; and the care management server is configured to restrict the content servers that one or both of the first user interface and the second user interface can access.

2. The system of claim 1, wherein the care management server is further configured to:
receive data concerning the status of the care recipient using automated user interface interactions via a telephone; and
send automatically generated notifications to the telephone based upon the analysis of the care management database.

3. The system of claim 1, wherein the first user interface is configured to:
display a game user interface;
record game performance; and
send game performance data to the care management server; and the care management server is further configured to:

receive game performance data from the first user interface and store the game performance data in the care management database;

analyze the game performance data to detect a decline of the care recipient's cognitive abilities; and send a notification to the second user interface in response to detecting the decline of the care recipient's cognitive abilities.

4. The system of claim 3, wherein the game user interface comprises cognitive skills exercise games or tools configured to facilitate cognitive interaction with the care recipient.

5. The system of claim 1, wherein the care management server is further configured to receive data concerning the status of the care recipient via a care receiver sensor.

6. The system of claim 1, wherein the care management server is further configured to communicate with one or more of the first user interface, the care receiver sensor, and a second user interface via the Internet.

7. The system of claim 6, wherein one or both of the first user interface and the care receiver sensor are configured to connect to the Internet.

8. The system of claim 1, wherein:

the care management server is further configured to receive data concerning the status of the care recipient via one or more of the first user interface and the care receiver sensor; and the care management server is configured to update one or more configuration settings of the first user interface and the care receiver sensor based upon the analysis of the data concerning the status of the care recipient in the care management database.

9. The system of claim 1, wherein at least one of the first user interface, the second user interface, and the care receiver sensor are configured to intermittently synchronize with the care management server.

10. The system of claim 1, wherein the care management server receive scheduling data from the first user interface.

11. The system of claim 1, wherein the care management database includes a database of pharmaceuticals.

12. The system of claim 1, wherein the care management server is further configured to:

analyze the data within the care management database to generate a timeline of upcoming notifications; and send the timeline of upcoming notifications to at least one of the first user interface and the second user interface, which displays a timeline of upcoming notifications.

13. The system of claim 1, wherein the care management server is configured to analyze the data within the care management database and send escalated notifications based upon the first care management instructions or second care management instructions stored in the care management database.

14. The system of claim 1, wherein the care management server is further configured to:

store data concerning the status of a plurality of care recipients in the care management database; and perform analytics to detect patterns that can be used to detect an increased likelihood of a particular status for a specific care recipient in the future.

15. The system of claim 1, wherein in the first mode of operation, the first user interface is laid over a portion of the television content such that the first user interface is presented regardless of the selected channel or input source and such that the presentation of the television audio and video content is not paused when the first user interface is presented by the first television set.

16. The system of claim 15, wherein the first user interface presented by the first television set in the first mode of operation comprises one or more of a message, a notification, or multimedia, the first user interface presenting the message, the notification, or the multimedia for a duration in a range of about five seconds to about 30 seconds.

17. The system of claim 1, wherein the first user interface being laid over the television content such that the first user interface is presented regardless of the selected channel or input source and such that, in a second mode of operation, the presentation of the television audio content is not paused when the first user interface is presented by the first television set.

18. The system of claim 17, wherein the first user interface presented by the first television set in the second mode of operation comprises one or more of a message, a notification, a reminder, multimedia, or visual content, the presentation of the television video content resuming responsive to completion of the second mode of operation.

19. The system of claim 1, wherein the first user interface being laid over the television content such that the first user interface is presented regardless of the selected channel or input source and such that, in a third mode of operation, the presentation of the television content is interrupted when the first user interface is presented by the first television set.

20. The system of claim 19, wherein the first user interface presented by the first television set in the third mode of operation comprises one or more of multimedia, video content, website, network content, two-way communication via real-time audio or video, video chat, or voice call, the presentation of the television audio and video content resuming responsive to completion of the third mode of operation.

21. The system of claim 1, wherein one or both of the first user interface and the second user interface is configured to facilitate interaction with a graphical user interface (GUI), application program (app), systems software, web application (web app), mobile app, or application software.

22. The system of claim 1, wherein the care management server is further configured to:

receive audio or video information from the care recipient via the personal computing device, the first user interface, telephone, app, web app, mobile app, or a communications network;

record the audio or video information; and store the audio or video information in the care management database.

23. The system of claim 22, wherein the audio or video information from the care recipient is narrative dictated by the care recipient.

24. The system of claim 1, wherein the system is configured to facilitate interactions between television sets and personal computing devices responsive to a user selection initiating the system via a channel tuner, input source selector, or application software.

25. The system of claim 1, wherein interactivity between television sets and personal computing devices is an embedded feature of the television sets such that an interaction between a given television set and a given personal computing device is initiated without the given television set receiving a user selection of an application from among a set of available applications visually presented via the given television sets.

26. A method for facilitating interactions between television sets and personal computing devices, the method being performed by one or more physical servers configured to be communicatively coupled with one or more television sets including a first television set and one or more personal computing devices including a first personal computing device, the care management server comprising a non-transitory storage medium having a care management database and machine-readable instructions embodied thereon, the care management server further comprising one or more hardware processors configured by the machine-readable instructions to perform the method, the method comprising:

receiving first care management instructions and data concerning the status of a care recipient associated with the first television set via a first user interface visually presented via a first hardware display of the first television set, the first user interface being laid over television content such that the first user interface is presented regardless of a selected channel or input source and such that, in a first mode of operation, the presentation of the television content is not paused when the first user interface is presented by the first television set;

receiving second care management instructions via a second user interface visually presented via a second hardware display of the first personal computing device, the second user interface being presented via an app executed by the first personal computing device;

storing the first care management instructions, the data concerning the status of the care recipient, and second care management instructions in the care management database;

analyzing the care management database in accordance with the care management instructions; and providing notifications to one or both of the first television set or the personal computing devices based upon the analysis of the care management database;

wherein the care management server is further configured to: receive data concerning the status of the care recipient via the first user interface; and send notifications to the second user interface based upon the analysis of the care management database; and wherein: one or both of the first user interface and the second user interface is configured to access content servers; and the care management server is configured to restrict the content servers that one or both of the first user interface and the second user interface can access.

27. The method of claim 26, further comprising facilitating interaction with a graphical user interface (GUI), application program (app), methods software, web application (web app), mobile app, or application software via one or both of the first user interface and the second user interface.

28. The method of claim 26, further comprising facilitating interactivity between television sets and personal computing devices, the interactivity being an embedded feature of the television sets such that an interaction between a given television set and a given personal computing device is initiated without the given television set receiving a user selection of an application from among a set of available applications visually presented via the given television sets.

* * * * *